(12) United States Patent
Ostyn et al.

(10) Patent No.: US 10,888,483 B2
(45) Date of Patent: Jan. 12, 2021

(54) SYSTEMS, DEVICES, AND METHODS FOR POSITION MONITORING AND MOTION COMPENSATION

(71) Applicant: VIRGINIA COMMONWEALTH UNIVERSITY, Richmond, VA (US)

(72) Inventors: Mark Ostyn, Henrico, VA (US); Siyong Kim, Richmond, VA (US); Woon-Hong Yeo, Richmond, VA (US); Thomas Dwyer, Richmond, VA (US); Melvin Rosario, Richmond, VA (US); Ross Cruikshank, Mechanicsville, VA (US); Daniel Martinez, Ashland, VA (US); Charles Cartin, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 205 days.

(21) Appl. No.: 16/069,235

(22) PCT Filed: Jan. 12, 2017

(86) PCT No.: PCT/US2017/013156
§ 371 (c)(1),
(2) Date: Jul. 11, 2018

(87) PCT Pub. No.: WO2017/123731
PCT Pub. Date: Jul. 20, 2017

(65) Prior Publication Data
US 2019/0015685 A1    Jan. 17, 2019

Related U.S. Application Data
(60) Provisional application No. 62/277,678, filed on Jan. 12, 2016.

(51) Int. Cl.
| A61G 13/12 | (2006.01) |
| A61G 13/02 | (2006.01) |
| A61B 6/00 | (2006.01) |

(52) U.S. Cl.
CPC .......... *A61G 13/121* (2013.01); *A61G 13/02* (2013.01); *A61G 13/12* (2013.01); *A61B 6/501* (2013.01)

(58) Field of Classification Search
CPC ........ A61G 7/002; A61G 7/005; A61G 7/008; A61G 7/012; A61G 7/015; A61G 7/018;
(Continued)

(56) References Cited

U.S. PATENT DOCUMENTS

| 3,206,188 A * | 9/1965 | Douglass, Jr. | ......... A61G 13/02 5/614 |
| 3,868,103 A * | 2/1975 | Pageot | .................. A61G 13/02 5/614 |

(Continued)

*Primary Examiner* — Robert G Santos
(74) *Attorney, Agent, or Firm* — W&C IP

(57) ABSTRACT

A motion compensation system includes a plurality of RF transmitters, a plurality of direction of arrival sensors, and a positioning table which together are usable to compensate for intrafraction motion of a patient during a medical procedure. The positioning table may be a secondary table arranged next to or above a primary table such as a radiotherapy couch, allowing for repositioning of part of patient such as the head and neck relative to a remainder of the body. The motion compensation system employs a direction of arrival sensor that includes rotating antenna elements in a configuration that improves the ease and accuracy of signal processing and analysis to identify the position of an RF transmitter affixed to a patient. The repositioning table has six degrees of freedom and is safe for use in imaging and radiation intensive environments.

6 Claims, 18 Drawing Sheets

(58) Field of Classification Search
CPC .......... A61G 7/05; A61G 13/02; A61G 13/04;
A61G 13/06; A61G 13/08; A61G 13/10;
A61G 13/12; A61G 13/121; A61B 6/04;
A61B 6/0407; A61B 6/0487; A61B 6/501
USPC .... 5/600, 601, 607–611, 621, 622; 378/208,
378/209, 20
See application file for complete search history.

(56) References Cited

U.S. PATENT DOCUMENTS

| | | | | |
|---|---|---|---|---|
| 3,900,906 A * | 8/1975 | Berthelsen | ............. | A61G 7/002 5/608 |
| 4,195,829 A * | 4/1980 | Reser | ............. | A61G 13/02 5/607 |
| 4,474,364 A * | 10/1984 | Brendgord | ............. | A61G 13/08 5/613 |
| 4,572,493 A * | 2/1986 | Hubert | ............. | A61G 13/04 5/608 |
| 4,736,736 A * | 4/1988 | Moers | ............. | A61H 1/0218 5/637 |
| 4,958,817 A * | 9/1990 | Heller | ............. | A61G 13/04 5/607 |
| 5,013,018 A * | 5/1991 | Sicek | ............. | A61G 13/02 5/601 |
| 5,299,334 A * | 4/1994 | Gonzalez | ............. | A61G 7/005 5/607 |
| 5,398,356 A * | 3/1995 | Pfleger | ............. | A61B 6/04 5/601 |
| 5,528,782 A * | 6/1996 | Pfeuffer | ............. | A61G 13/02 108/147 |
| 5,621,933 A * | 4/1997 | Knapp | ............. | A61G 7/018 5/607 |
| 6,094,760 A * | 8/2000 | Nonaka | ............. | A61B 6/0487 5/601 |
| 6,269,499 B1 * | 8/2001 | Amir | ............. | A61B 6/04 5/600 |
| 6,416,219 B1 * | 7/2002 | Pflaum | ............. | A61G 13/02 378/209 |
| 6,505,363 B2 * | 1/2003 | Davis | ............. | A47C 17/80 296/190.02 |
| 6,640,363 B1 * | 11/2003 | Pattee | ............. | A61G 13/04 5/601 |
| 6,865,411 B2 * | 3/2005 | Erbel | ............. | A61B 6/0421 600/407 |
| 7,120,223 B2 * | 10/2006 | Nafstadius | ............. | A61B 6/04 378/20 |
| 7,181,792 B2 * | 2/2007 | Nakamura | ............. | A61B 6/0487 5/601 |
| 7,373,676 B2 * | 5/2008 | Markovic | ............. | A61N 5/1049 378/209 |
| 7,591,035 B2 * | 9/2009 | Guo | ............. | A47C 21/006 5/11 |
| 7,653,952 B2 * | 2/2010 | Guo | ............. | A47C 21/006 5/600 |
| 7,818,838 B2 * | 10/2010 | Erbel | ............. | A61N 5/103 5/601 |
| 8,242,465 B2 * | 8/2012 | Iwata | ............. | G01N 23/00 250/491.1 |
| 8,674,326 B2 * | 3/2014 | Iwata | ............. | G01N 23/00 250/491.1 |
| 8,789,223 B2 * | 7/2014 | Erbel | ............. | A61N 5/103 5/601 |
| 8,966,686 B2 * | 3/2015 | Wiggers | ............. | A61N 5/1049 5/608 |
| 9,456,947 B2 * | 10/2016 | Dawson | ............. | A61G 13/121 |
| 10,206,841 B2 * | 2/2019 | Soltermann | ............. | A61G 13/04 |
| RE47,588 E * | 9/2019 | Erbel | ............. | A61N 5/103 |
| 2002/0078500 A1 * | 6/2002 | Davis | ............. | A47C 17/80 5/118 |
| 2002/0120986 A1 * | 9/2002 | Erbel | ............. | A61N 5/103 5/601 |
| 2004/0057557 A1 * | 3/2004 | Nafstadius | ............. | A61B 6/04 378/209 |
| 2005/0028280 A1 * | 2/2005 | Nakamura | ............. | A61B 6/04 5/601 |
| 2005/0138732 A1 * | 6/2005 | Erbel | ............. | A61N 5/103 5/601 |
| 2007/0003014 A1 | 1/2007 | Boese et al. | | |
| 2007/0032795 A1 * | 2/2007 | Schloesser | ............. | A61N 5/1049 606/130 |
| 2007/0143923 A1 * | 6/2007 | Guo | ............. | A47D 9/02 5/608 |
| 2007/0143924 A1 * | 6/2007 | Guo | ............. | A47C 21/006 5/608 |
| 2008/0212737 A1 | 9/2008 | D'Souza et al. | | |
| 2010/0282983 A1 | 11/2010 | Wright et al. | | |
| 2011/0015521 A1 | 1/2011 | Faul et al. | | |
| 2011/0046481 A1 | 2/2011 | Mate et al. | | |
| 2011/0088166 A1 * | 4/2011 | Erbel | ............. | A61N 5/1049 5/601 |
| 2011/0215259 A1 * | 9/2011 | Iwata | ............. | G01N 23/00 250/491.1 |
| 2012/0248331 A1 * | 10/2012 | Iwata | ............. | G01N 23/00 250/453.11 |
| 2013/0111668 A1 * | 5/2013 | Wiggers | ............. | A61B 6/0487 5/608 |
| 2013/0345718 A1 | 12/2013 | Crawford et al. | | |
| 2015/0045676 A1 | 2/2015 | Dawson et al. | | |
| 2015/0202073 A1 * | 7/2015 | Zacharopoulos | ..... | A61F 5/3707 128/845 |
| 2018/0193216 A1 * | 7/2018 | Soltermann | ............. | A61G 13/04 |
| 2019/0015685 A1 * | 1/2019 | Ostyn | ............. | A61G 13/121 |
| 2020/0281787 A1 * | 9/2020 | Ruiz | ............. | B25J 11/009 |

* cited by examiner

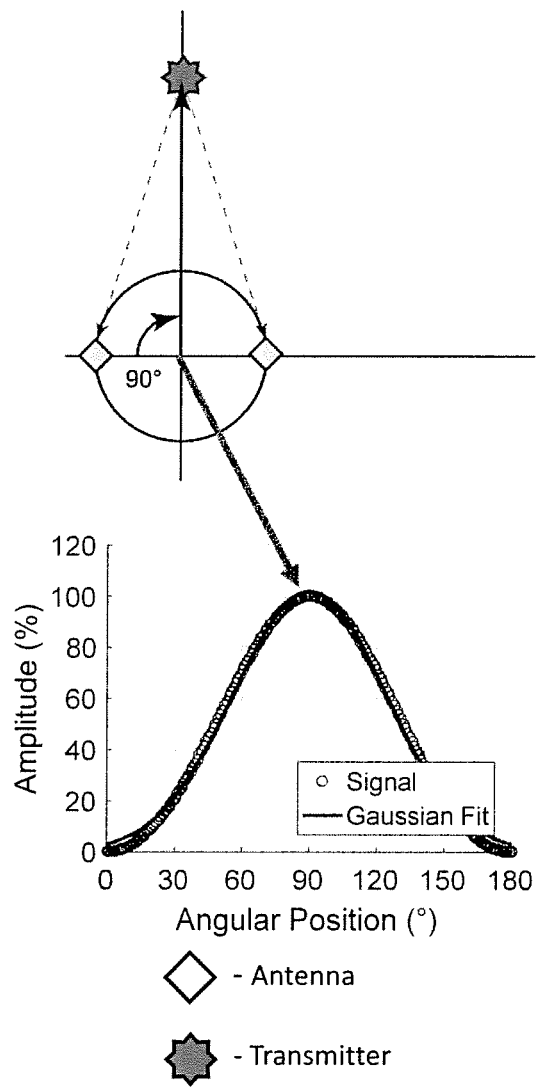 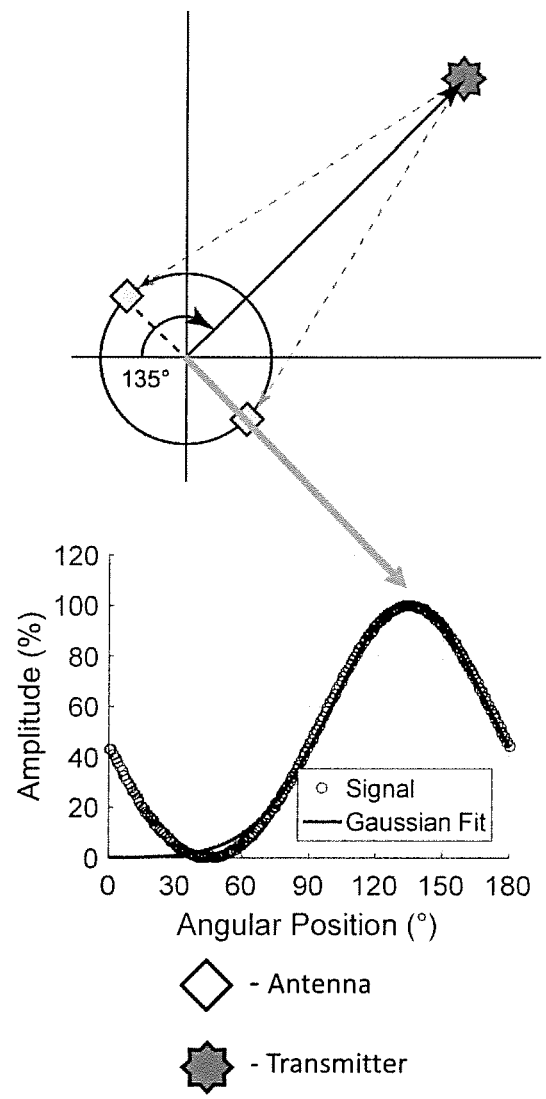
Figure 13A
Figure 13B

SYSTEMS, DEVICES, AND METHODS FOR POSITION MONITORING AND MOTION COMPENSATION

FIELD OF THE INVENTION

The invention generally relates to systems and methods for reducing spatial uncertainties during position sensitive procedures and, in particular, systems and methods for addressing intrafraction motion during head and neck radiotherapy, for example.

BACKGROUND

Many cancers in the head and neck are treated with highly conformal radiotherapy, which includes steep dose gradients between disease sites and healthy tissue. Conformal dose strategies include intensity modulated radiotherapy (IMRT) and stereotactic body radiotherapy (SBRT). This type of treatment modality demands accurate setup and minimal patient movement during treatment delivery. The importance of proper patient positioning both at setup and throughout the treatment delivery cannot be overstated. In the modern convention, clinicians utilize thermoplastic masks to immobilize patients for head and neck treatment sites. However, research suggests that these masks do not fully arrest patient motion, with extreme cases showing maximum translational motions up to 7.4 mm along a single axis and maximum rotational motions up to 8.2° about a single axis. While technology exists to track patient motion during treatment delivery, existing methods rely on optical information which require direct line of sight (LOS) and do not perform well with the deformable skin surface near the face.

External beam radiation therapy is one of the most significant tools available in modern cancer treatment. Linear accelerators (linacs) generate high-energy photons and careful planning directs the output into tumors in patients. These x-rays introduce an ionizing dose of radiation into matter along the path of the beam. Dose may be defined as the amount of energy deposited per unit mass. The received dose damages DNA at the molecular level, which increases the likelihood of cell death. Healthy tissue along the beam path is spared from receiving excessive dose by spreading dose delivery over several beam angles. FIG. 1A illustrates this technique. Beams 11 each have a different beam angle in order to spare non target tissue from dangerous levels of radiation. The beams 11 only overlap at the target site which aligns perfectly with a tumor under ideal circumstances. Tissue sparing comes at the cost of delivering low doses to a greater volume of healthy tissue, but this risk is accepted by medical practitioners and patients because healthy tissue may repair light radiation-caused damage. Most treatments deliver the cumulative dose in a series of fractions over the course of 2-8 weeks, with each fraction taking 15-30 minutes to deliver, which grants healthy tissue sufficient time for DNA repair.

New delivery techniques, such as intensity-modulated radiation therapy (IMRT) or volume-modulated arc therapy (VMAT), allow precise delivery of the dose to a set volume in space, conforming to the shape of the tumor and sparing healthy tissue from potential damage. These types of treatments are often characterized by steep dose gradients between the target region and normal tissue, which necessitates accurate positioning during treatment. Precise information about the position, orientation, and motion of the tumor is often unknown during dose delivery, therefore oncologists prescribe a volumetric margin of necessary size to ensure probabilistically delivering the prescribed dose to a sufficient percentage of the disease site volume, for a given level of spatial uncertainty. Larger margins increase the amount of healthy tissue receiving cell-lethal dose and may overlap with critical organs such as the brain, lungs, heart, bowels, or other organs necessary for normal bodily function. Additionally, even in bulk tissue large doses to healthy tissue can promote further cancers later in life. Thus, modern treatment planning requires sufficiently large margins to ensure tumor coverage as well as necessarily small margins to avoid delivering excess dose to healthy tissue.

The magnitude of the spatial uncertainties must be well known and minimized whenever possible. The most notable sources of uncertainty are improper alignment of the patient with the prescribed field, an example of interfraction setup error, and movement of the patient during treatment delivery, often called intrafraction motion. FIG. 1B illustrates a subject 13 receiving radiotherapy treatment of a brain tumor. The subject 13 lies on his or her back on a treatment couch 14 with the radiotherapy beams emitted from linear accelerator 15. FIG. 1C illustrates the same subject 13 after the subject has moved his head relative to the beam, an intrafraction motion. The beam is delivered to the same point in space, but the intended treatment site is out of alignment. Setup errors have long been minimized by employment of immobilization equipment and alignment of fiducial markers with static laser grids, but intrafraction motion has only recently been studied.

Dosimetrists define the target volume in treatment planning software based on computed tomography (CT) scans of the patient. Cell-lethal doses are prescribed to the disease site and surrounding volumetric margins, which compensate for positioning uncertainty. Precise and accurate imaging techniques cannot determine the exact position and orientation of interior anatomy during treatment delivery. Therefore, oncologists prescribe a margin of necessary size to ensure probabilistically delivering the prescribed dose to a sufficient percentage of the disease site, for a given level of spatial uncertainty. Larger margins increase the amount of healthy tissue receiving cell-lethal dose, and may overlap with critical organs, such as the brain, lungs, heart, bowels, or other organs necessary for normal bodily function. Further, even in bulk tissue, large doses to healthy tissue can promote further cancers later in life. Therefore, adequately ensuring tumor coverage requires sufficiently large prescribed margins, as well as necessarily small margins in order to avoid delivering excess dose to healthy organs and tissue.

Several methods exist to reduce these spatial uncertainties. The combination of methods varies by disease location site and departmental preference. The use of immobilization equipment ensures setup reproducibility and reduces intrafraction motion, but does not fully eliminate either of these problems. Radiographic systems such as cone-beam CT, stereoscopic x-ray, orthogonal x-ray, fluoroscopy, and portal imaging provide precise information about the positioning and orientation of interior anatomy, but also deliver extra dose to the patient when used, which limits their utility to monitoring intrafraction motion. Ultrasound provides realtime views of interior anatomy without dosimetric impact, but lack the soft tissue contrast necessary accurate delineation of tumor from normal tissue. Therefore, ultrasound only measures relative motion of significant density heterogeneities, such as a bone-tissue or blood-tissue interface.

Optical systems such as surface tracking or marker tracking have been used to monitor intrafraction motion in several disease sites, including head and neck, prostate, and breast, with surface mapping stereoscopic camera systems or with infrared (IR) reflective marker systems. Surface imaging techniques create a map of the 3D external contour of a patient's surface using cameras at multiple viewing angles. An image registration program then compares the surface map seen by the camera system to a reference contour map, which may be obtained by either the camera system or the most recent planning CT image. The computer calculates the rigid-body transformation needed to register the current contour to the reference contour, which corresponds to intrafraction motion. By knowing the range of magnitude of this motion, oncologists may prescribe appropriately sized margins.

Unfortunately, surface imaging systems have notable shortcomings. Firstly, they require line-of-sight (LOS) on the region of interest. This limits placement and positioning of sensors and could mean that garments may require removal to accurately image. Requiring patients to be exposed could make a patient uncomfortable, which could promote further movement. Secondly, the system assumes that a registration between the reference and current image is always possible, which is not always the case. The body easily deforms for a number of causes that are common in the clinic including motion, weight loss, and tumor shrinkage. These deformations can lead to inaccurate registrations, which can misestimate the magnitude of motion. Thirdly, the single rigid body assumption may not be appropriate for all regions of the body, especially the neck, which derives its position and orientation from the relative attitudes of the thorax and head. Lastly, surface imaging systems assume that observed motion of the area of interest corresponds exactly to motion of the interior anatomy, which may or may not be true. In sum, these systems require line of sight, are not robust against changes in patient size and shape, detrimentally assume a single rigid body irrespective of body area, and track movements that may not correlate well with interior anatomy.

IR-reflective systems work by observing infrared light reflected off spherical retroreflectors attached to a patient in a rigid, known pattern. Deviations in the observed pattern correspond as translations and rotations of the area of interest. While this type of system is capable of quickly measuring intrafraction motion, and is resistant against surface deformations, IR reflective systems face similar shortcomings as surface mapping techniques, such as requiring line of sight, assuming a single rigid-body, and assuming that motion of the markers corresponds to motion of the interior anatomy. Further, markers cannot attach directly to the patient, which exacerbates this problem. Instead, the reflectors typically attach to an external surrogate, such as an immobilization mask or bite plate.

Active motion compensation systems can be used to suppress or counteract patient motion using active mechanical components. Early attempts at active motion compensation systems have relied on conventional robotic construction, utilizing metal structural components and stepper motors to achieve precise motion. However, the nature of x-ray interactions makes these elements poor candidates in radiation therapy. Significant quantities of metal within the treatment field can significantly contribute to beam attenuation and scatter, which may interfere with planned dose distributions, or produce photon starvation artifacts in setup cone beam computed tomography imaging, as well as Compton blurring in planar radiographic setup imaging. Furthermore, conventional stepper motors also inherently render any electrical motor incompatible with the strong magnetic fields utilized in magnetic resonance imaging.

SUMMARY

According to some embodiments, a localization system uses direction of arrival (DOA) measurements in an RF sensor network to monitor the position and motion of specific points in near real-time. New RF localization systems overcome the main weaknesses of existing intrafraction motion tracking systems. In some medical applications, exemplary systems angulate skin-wearable transmitters on a patient. Use of transmitter beacons as points of interest facilitates distinguishing between each point, allowing for tracking of multiple rigid bodies. This technique allows a precise localization of transmitters, mounted on a patient, without demanding strict timing such as GPS. The analog nature of some exemplary systems further grant increased precision in measurement. Disclosed systems, devices, and methods are robust against changes in patient anatomy and provide real-time tracking of changes in complex patient positioning. Furthermore, they do not require line-of-sight detection and avoid extra radiation dose to a patient. Exemplary localization systems include tracking each transmitter in 3D, e.g., by combining the measurements from two orthogonal 2D localization subsystems.

Some exemplary positioning sensor networks or systems comprise a series of skin-wearable transmitters gently affixed to a patient (e.g., the patient's skin) and an external sensor network that tracks patient position and attitude in real time through estimate of the transmitters' positions. RF waves have intrinsic advantages over other photonic means because radio waves readily propagate through many materials and do not deliver any radiation dose to matter. Further, by attaching the transmitters at strategic anatomical sites, the system is resilient against skin deformation issues encountered with optical systems.

Some exemplary sensors (e.g., a sensor modules) are disclosed which comprise a rotating array platform together with antenna elements (e.g., configured in pairs). The sensors find a direction of patient-mounted transmitters in a 2D plane with high accuracy (e.g., within ~0.1°), and multiple sensors together are usable to find transmitter positions in 3D space. A network of sensor modules is usable to find the location of transmitters based on the combined direction measurements of the respective sensor modules.

According to a further aspect of some embodiments, active motion compensation systems and methods are provided which compensate for intrafaction motion during medical procedures such as radiotherapy and medical imaging. In some embodiments, systems are provided which reposition a patient's head separately from the rest of the body if significant motion occurs.

An exemplary motion compensation system comprises two major components: a wireless positioning sensor network and a mechanical positioning table that interact as a negative feedback loop to reduce or eliminate spatial uncertainties or changes during position sensitive procedures. An exemplary mechanical positioning table is, for example, a mechanical 6-dimension, radio-compatible, plastic-based table. The table may be attached to a patient's headrest, and it performs compensating movements in response to patient head motion detected by the sensor network.

Simulation study and experimental validation of table mechanics demonstrate the structural reliability for in vivo research and clinical use. Implementation of a feedback-based control system in conjunction with position sensing systems enables active motion compensation in head and neck radiotherapy. Exemplary robotic systems such as a positioning table are compatible with localization/position sensing systems disclosed herein as well as existing systems like AlignRT or ExacTrac (BrainLab AG, Feldkirchen, Del.).

An exemplary positioning table comprises a support surface, sliding blocks, tracks, linkages, and joints with at least two degrees of rotational freedom (e.g., pitch and yaw). The joints may be, for example, pivoting hinges or ball and socket joints. A positioning table may further include a powertrain connecting external motors with the sliding blocks such that rotational motion of a motor causes a sliding block mounted in the linear track to translate along the track, thereby changing a position of one or more of the linkages. For compatibility with various medical procedures, some exemplary embodiments use metal-less materials for the plate, sliding blocks, linear tracks, linkages, and joints.

In some exemplary embodiments, a (secondary) positioning table is configured to support a specific part of the patient's body during the medical procedure while a primary positioning table (e.g., a radiotherapy couch) is configured to support up to an entirety of the patient during the medical procedure. A control device such as one or more computers are configured to move the secondary positioning table with respect to the primary positioning table to adjust a position of a specific part of the patient's body relative to a remainder of the patient's body. The secondary positioning table may be positioned on or connected/attached to the primary positioning table.

BRIEF DESCRIPTION OF THE DRAWINGS

FIG. 13A shows spatial geometry of a single sensor at the selected location of 90° with respect to the coordinate system and the sensor's signal response for one-half revolution.

FIG. 13B shows spatial geometry of a single sensor at the selected location of 135° with respect to the coordinate system and the sensor's signal response for one-half revolution.

DETAILED DESCRIPTION

Figure 1A:
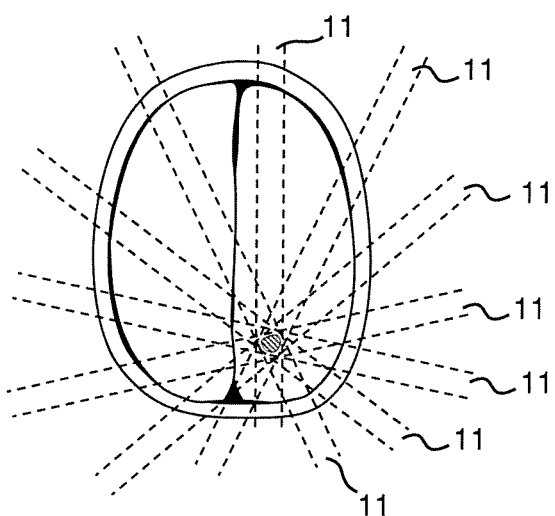
FIG. 1A is an example of conformal radiotherapy for the treatment of a brain tumor.
Figure 1B:
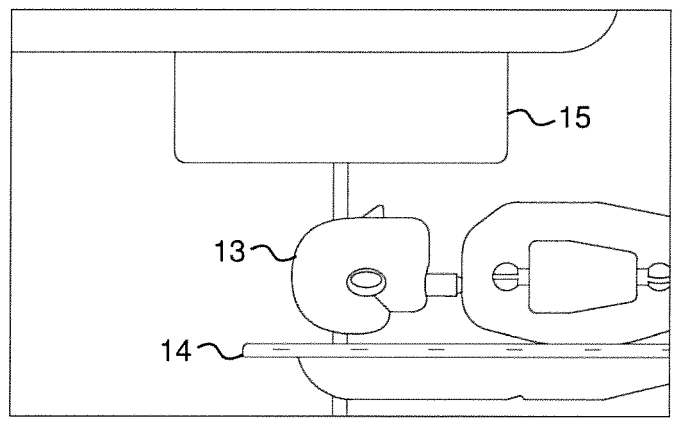
FIG. 1B shows a patient receiving external beam radiation therapy for brain cancer.
Figure 1C:
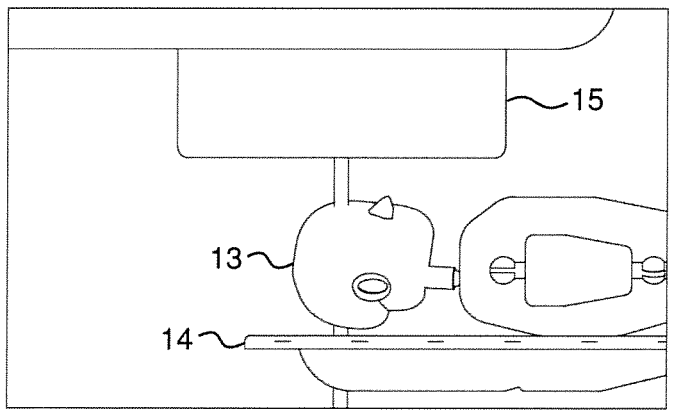
FIG. 1C shows an example of motion error relative to planned delivery.
Figure 2A:
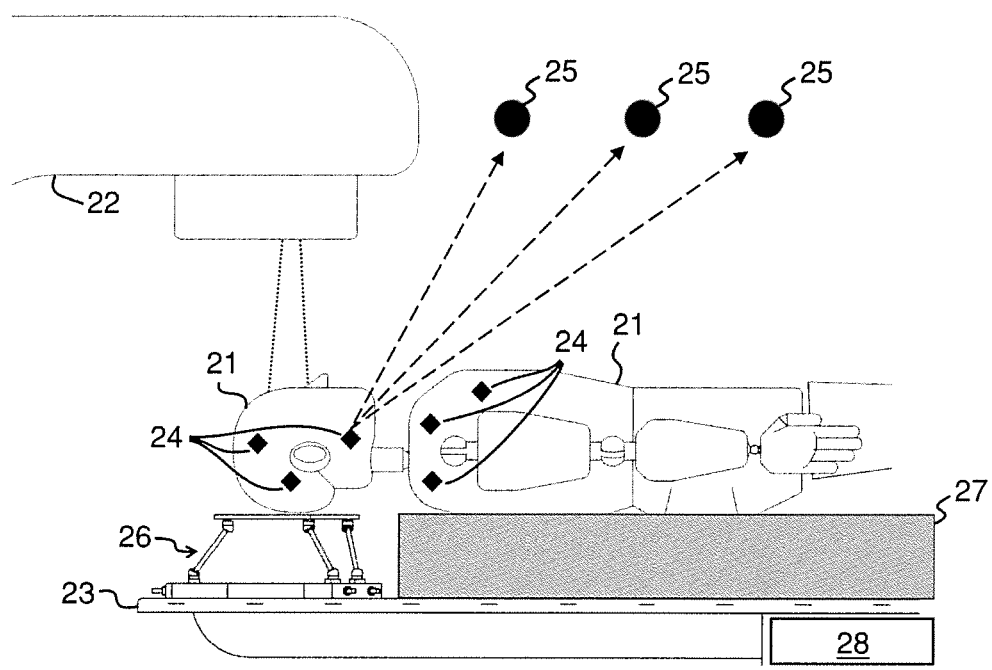
FIG. 2A shows a schematic of a radiotherapy system in combination with an active motion compensation system.

FIG. 2A is a schematic of a radiotherapy system together with an (active) motion compensation system. A patient 21 is positioned on a traditional treatment couch 23 under a linear accelerator treatment head 22. The motion compensation system comprises triplets of transmitters 24 in a skin-wearable form, and a network of direction of arrival (DOA) sensors 25. Each triplet of transmitters (also referred to as beacons) is attached to fixed landmarks on a rigid body. In a known (e.g., preconfigured) sequence, each transmitter 24 transmits a pulsed sine wave operating at one or more specified frequencies. For instance, in an Example below, transmitters operate at a frequency of 1.5 GHz. The emitted wave from the transmitters may alternatively have a single wavelength or be a combination of two, three, or more than three wavelengths.

In some embodiments, the sensors 25 are separated into two groups: one group configured to localize each wave from the transmitters in the horizontal plane, and one group configured to localize each wave in an (arbitrary) vertical plane. Each sensor 25 measures the estimated direction of arrival of each pulse sequence, and each group performs a least-squares estimate of the wave's point of origin in their respective planes of interest. The results are combined to find a three-dimensional estimation of the positions of each sensor 25 in three-dimensional space. The determined positions of the transmitters 24 in three-dimensional space indicate the actual position of the patient or part of the patient (e.g., the head, or the neck, or the shoulders) in three-dimensional space. The processing and analysis of signals detected by the sensors 25 may be performed by circuitry configured for this purpose and/or one or more computers. The circuitry and computer(s) provided for signal processing and analysis may be installed within each sensor 25. It may also or alternatively be provided at a central location, such as a central computer or server which receives signals from all of the respective sensors 25 that are networked together for the shared purpose of localizing one or more transmitters. The same or different circuitry and computer(s) that support the sensor network may serve as a control device for controlling and moving the secondary positioning table with respect to the primary positioning table to adjust a position of the specific part of the patient's body relative to a remainder of the patient's body. A computing and/or control device 28 is shown generally in FIG. 2A and is representative of circuitry, a computer, or computers which performs or may perform data processing described herein and control operations (e.g., act as a control device of positioning table 26).

Each triplet of transmitters 24 is interpreted as a rigid body, whose position and orientation may be calculated by the relative positions of each transmitter 24 in the triplet. The initial positions of the transmitters 24 are recorded as an initial or reference position set. The positions of the transmitters 24 are then monitored over time. If the position or orientation of the rigid body on the table moves out of place over a specified threshold value, the positioning table 26 is signaled to move to compensate. After the compensating movement, the positions of the rigid body are measured for confirmation. The process repeats until the end of a radiotherapy session. To compensate for the extra height of the positioning table 26, one or more vertical supports 27 may be included for adjusting the height of a remainder of the patient's body relative to the treatment couch 23.

Figure 2B:
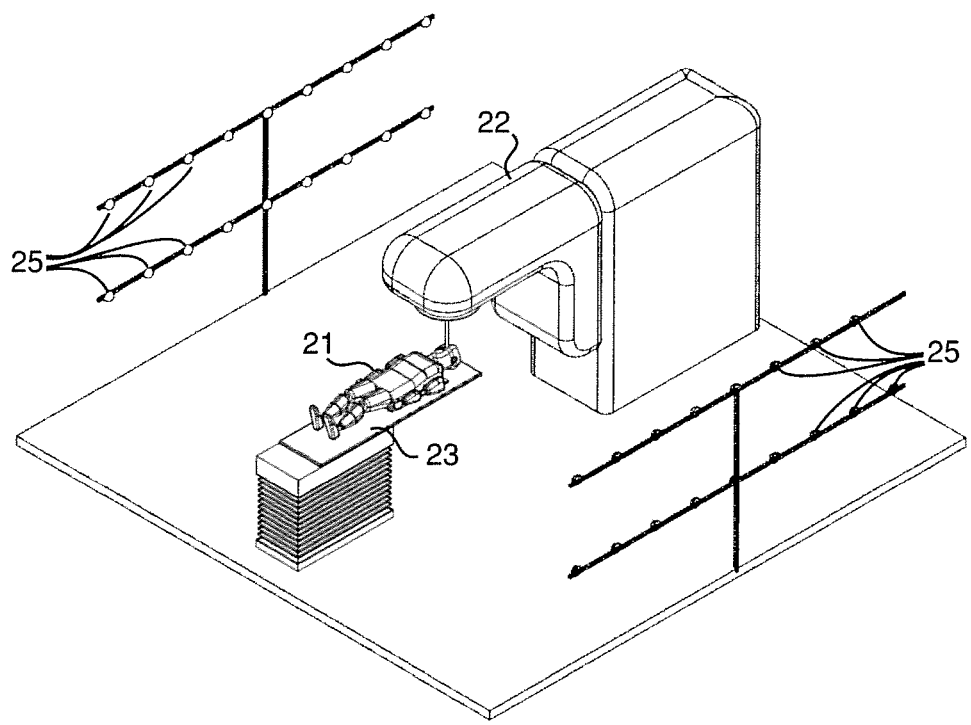
FIG. 2B shows a three-dimensional rendering of a radiotherapy system in combination with a sensor grid comprising four rows of sensors positioned to the sides of the treatment site.

FIG. 2B shows a three-dimensional rendering of the radiotherapy system and motion compensation system represented in FIG. 2A. In this example, the motion compensation system includes a sensor grid comprising four rows of sensors 25 positioned to the sides of the treatment site and patient 21. Only a portion of the sensors 25 are labeled in the figure to avoid cluttering the image. The four-rowed sensor grid is one exemplary configuration for a network of sensors 25. Other network configurations are possible in alternative embodiments. Examples include random grid formations, single rows, two or more rows, three or more rows, and rows having different numbers of sensors compared to other rows. Further alternatives include random distributions and hemispherical distributions which center at the cluster of transmitters on the patient. As in FIG. 2A, the patient is lying on a treatment couch 23 under a linear accelerator head 22. Owing to the viewing angle of the rendering, sensors affixed to the patient 21, the vertical support 27, and the positioning table 26 of FIG. 2A are not shown in FIG. 2B.

Prior to discussing specific components and functionalities of the sensors 25, it may be helpful to discuss the principle distance measuring techniques employed by many exemplary embodiments. Two alternative techniques for distance measuring are lateration and angulation.

Figure 3A:
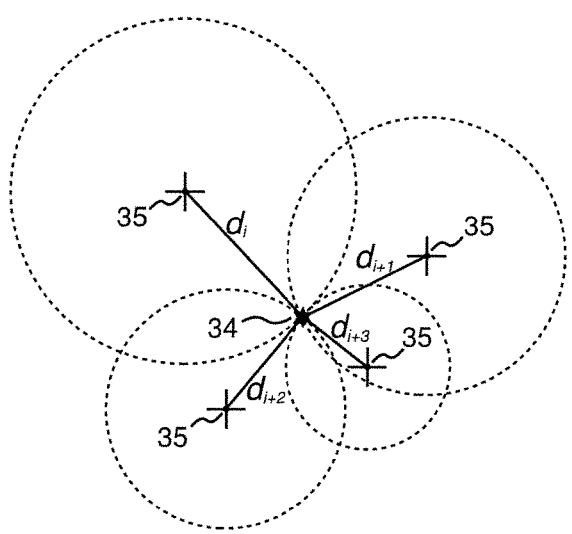
FIG. 3A is an example of locating a point in space by lateration.

FIG. 3A generally illustrates a lateration technique. Lateration based on distance measurements is one technique for estimating a position in space. In FIG. 3A, four sensors 35 are used together to determine the position of a single transmitter 34. It is determined for each sensor 35 that the transmitter 34 is a respective distance of $d_i$, $d_{i+1}$, or $d_{i+3}$ away. A point in space which meets all four distance constraints is determined to be the actual position of the transmitter 34.

Figure 3B:
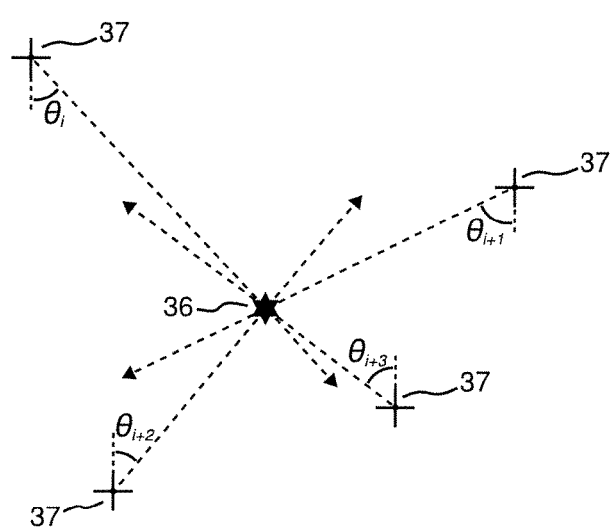
FIG. 3B is an example of locating a point in space by angulation.

FIG. 3B generally illustrates an angulation technique. Angulation is a separate technique from lateration and is based on direction-of-arrival (DOA) measurements. In FIG. 3B, four sensors 37 are used together to determine the position of a single transmitter 36. A separate vector defines the path between each sensor 37 and the transmitter 36. Each vector has a respective angle of $\theta_i$, $\theta_{i+1}$, $\theta_{i+1}$, $\theta_{i+2}$, or $\theta_{i+3}$. The vectors are combined to determine the position of the transmitter 36. DOA measurements are advantageous over lateration because angulation-based positioning does not require extremely precise calibrated clock synchronization, unlike lateration. However, reliable techniques that may accurately measure the DOA of an RF wave have been absent until recently with the advent of phase-based correlations.

In any positioning technique, it is very unlikely that a closed solution exists for the measurements made. In angulation techniques specifically, it is very unlikely that all direction vectors will intersect at the exact same point in space. To solve the problem of having no closed solution, many embodiments employ least-squares estimates performed by one or more computers. The error in an estimation is the vector difference between a true position of a transmitter and the estimated position of the transmitter. A Monte Carlo simulation is able to estimate the magnitude of the error based on the input parameters, physical relationship between point of interest and points of measure, number of points of measure, and angular resolution of DOA measurement. Such a simulation is detailed below under the subheader of "EXAMPLE 1".

One approach to measuring the direction of arrival of an RF wave is by comparing the phase difference of an RF wave between elements of static antenna arrays. In static antenna arrays, the sensors 25 (FIGS. 2A and 2B) do not rotate or otherwise move. Simultaneous signal amplitude is compared between two or more elements (i.e., sensors 25) of the static antenna arrays to infer the DOA of an incoming RF wave, based on trigonometry and wave mechanics. According to some embodiments of the invention, the sensors 25 illustrated in FIGS. 2A and 2B are static sensors (e.g., they do not contain or involve moving parts) that together form a static antenna array or arrays.

In some preferred embodiments, antenna arrays are not static but instead have one or more moving antenna elements (e.g., rotating antenna elements). In some embodiments all of the antenna elements are moving, in particular rotating. Still other embodiments have a combination of static and moving antenna elements and/or arrays.

Figure 4A:
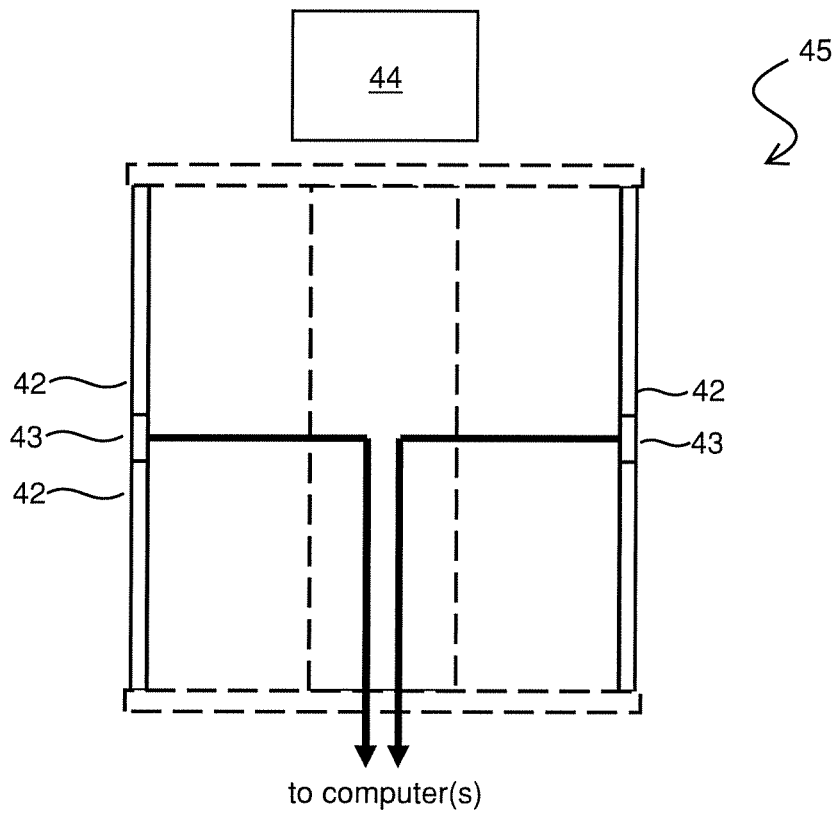
FIG. 4A is a sectional side view of a schematic diagram of a radio frequency (RF) direction of arrival (DOA) sensor.
Figure 4B:
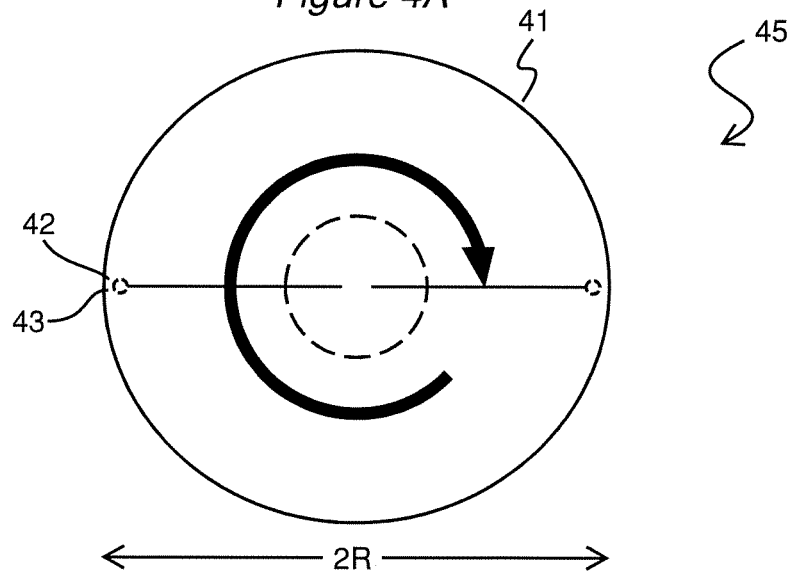
FIG. 4B is a top view of a schematic diagram of a radio frequency (RF) direction of arrival (DOA) sensor consistent with FIG. 4A.

FIGS. 4A and 4B are schematic diagrams of a rotating sensor 45 according to some exemplary embodiments. The sensor 45 is a radio frequency (RF) direction of arrival (DOA) sensor. Each sensor 45 of an exemplary rotating antenna array comprises a rotating array platform 41 and one or more pairs of antenna elements. As used herein, an antenna element may also be interchangeably referred to as a receiver. Each pair of antenna elements comprises a first antenna element for detecting a RF wave and a second antenna element for detecting the same RF wave. A single pair of antenna elements can be used for detecting a wave of a particular frequency. Alternatively, two pairs of antenna elements may be used in a dual frequency antenna for a RF wave that is a combination of two frequencies (e.g., 1.5 GHz and 47 GHz). Accordingly, a dual frequency antenna comprises four receiving antenna elements, separated into two pairs.

Whatever the number of pairs, the antenna elements are mounted to or within the platform 41. Each pair of antenna elements is attached such that the antenna elements of any given pair have different positions about an axis of rotation of the platform. The platform 41 in the illustrated embodiment of FIGS. 4A and 4B has a cylindrical shape, although other shapes are also acceptable. For a dual frequency antenna embodiment, two of the receiving antenna elements 42 which form a pair operate at a low primary (carrier) frequency (e.g., 1.5 GHz), and two of the receiving antenna elements 43 which form another pair operate at a high frequency (e.g., 47 GHz). Each frequency pair is arranged to be at opposite ends of the circular, cylindrical mount 41. In other words, first and second antenna elements of each pair of antenna elements are separated by the diameter of the platform on opposite sides of the axis of rotation. The platform is generally a body or frame made of suitable material like plastic or metal. The platform supports the antenna elements and permits a distance between separated antenna elements to be fixed at a predetermined value. In some exemplary embodiments, the diameter 2R is preselected to be half the wavelength of the low frequency RF carrier wave which the sensor 45 is configured to detect. The antenna elements 42 and 43 connect to one or more computers through the central shaft of the cylinder platform. An external motor 44 rotates the cylindrical mount 41 at a specified (i.e., predetermined) angular speed. Rotation is along the long central axis of the cylindrical mount 41, as illustrated by the large black arrow in FIG. 4B.

Figure 5A:
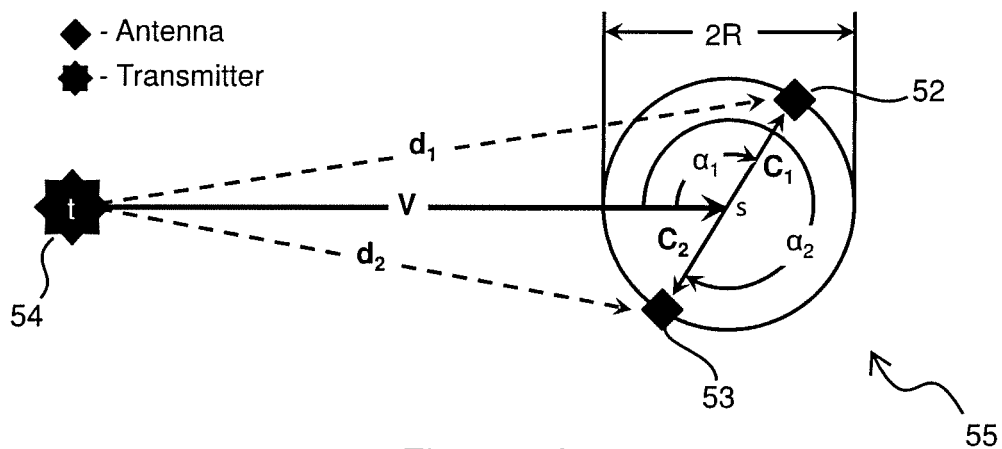
FIG. 5A is a geometric representation of single sensor used to find the direction vector V of a transmitter.

FIG. 5A is a geometric representation of single DOA sensor 55 used to find the direction vector V of a transmitter 54. An exemplary DOA sensor 55 comprises at least one pair of antenna elements, including a first antenna element 52 and a second antenna element 53 placed at opposite sides of a cylinder platform (diameter: 2R) which rotates around the central axis of the cylinder. The cylinder is represented as a circle. The relationship between the signals received by the antenna elements 52 and 53 determines a direction vector toward the patient-mounted transmitter 54 in a 2D plane. One or more computers are generally provided for comparing the respective signals received with each antenna element and determining the direction vector based on the comparison. Suitable computers include, for example, independent general purpose computers or special purpose computers which may be integrated within each of the respective sensors or be provided externally.

Each transmitter 54 affixed to a patient emits an RF wave (e.g., a sine wave) for a given duration. The RF wave consists of one or more frequencies (e.g., 1.5 GHz, or 1.5+47 GHz) as a compromise between antenna spatial constraints and available spectra. In some embodiments, a single frequency is used. In other embodiments, dual frequencies are used. The vector V between a center of the transmitter 54 and a center of rotation of the sensor 55 remains constant. The distances between the transmitter 54 and the antenna elements 52 and 53, such distances being represented in the drawing as $d_1$ and $d_2$ respectively, vary cyclically with the rotation of the sensor 55. As the sensor 55 rotates, one or more computers multiply the signals from two antenna elements together and measure the resultant amplitude. The distances $C_1$ and $C_2$, which are the respective distances from the axis of rotation to the separate antenna elements 52 and 53, are preferably equal in magnitude. However, alternative embodiments may be provided in which $C_1$ and $C_2$ are not equal. Angular rotation of each antenna element can be described according to a common radial axis of the platform. In FIG. 5A, antenna element 52 is at a rotational position of $\alpha_1$, and antenna element 53 is at a rotational position of $\alpha_2$. It is preferable that $\alpha_1$ and $\alpha_2$ differ by 180° at any given time. However, alternative embodiments may be provided in which $\alpha_1$ and $\alpha_2$ have a different relationship.

Figure 5B:
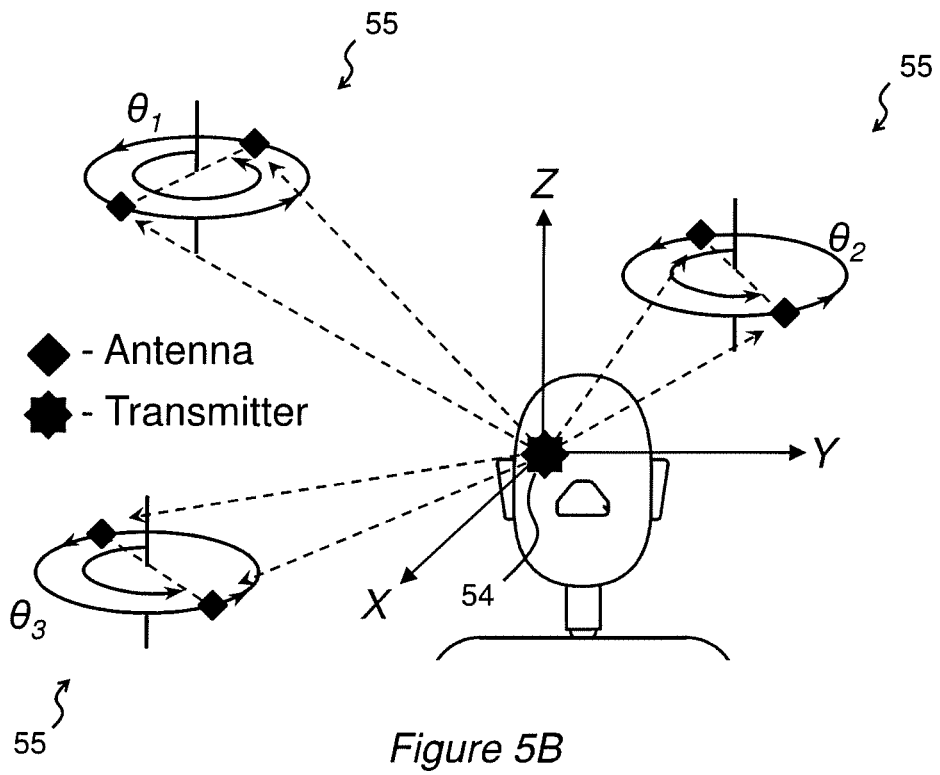
FIG. 5B shows a network of sensors used in parallel to find the location of the transmitter positioned on a patient.

FIG. 5B shows a network of three sensors 55 used in parallel to find the location of the transmitter 54 positioned on a patient's head. A group of sensors finds the direction toward the transmitter in the plane of the sensors (i.e., the plane in which the antenna elements are rotating). In FIG. 5B the three sensors 55 determine the direction of arrival in the xy-plane. Another group of sensors is then provided to determine the direction of arrival in a vertical plane (e.g., the yz-plane or the xz-plane).

Figure 6:
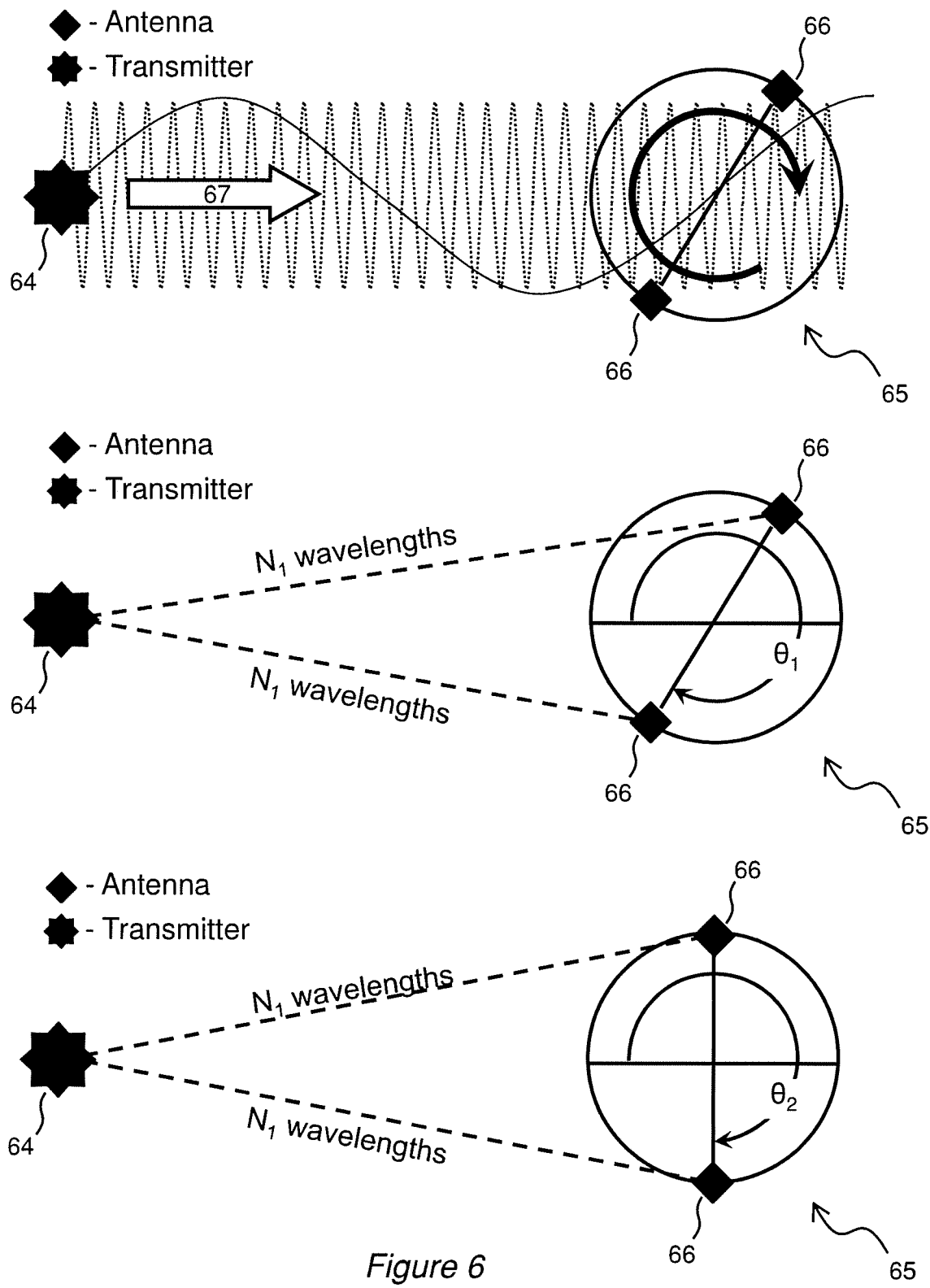
FIG. 6 is an operational schematic of a DOA sensor.

FIG. 6 is an operational schematic of a DOA sensor 65. Each transmitter 64 emits a RF wave 67 operating at one or more frequencies (e.g., 1.5 GHz, or 1.5 GHz and 47 GHz). FIG. 6 illustrates a combination of two waves, one of a high frequency and one of a low frequency. As the sensor 65 rotates through the wave 67, the antenna element pairs 66 receive the wave signals. For a dual frequency embodiment, there are two antenna elements at each square block 66 in order to detect/receive both the small frequency signal and the high frequency signal. As used herein, "low" and "high" may simply be used to describe the frequencies relative to one another (i.e., the low frequency is the lower frequency of the two frequencies, and the high frequency is the higher frequency of the two frequencies). In some embodiments, each transmitter 64 emits one wave of a given frequency instead of two waves operating at separate frequencies, in which case an individual antenna element is used at each square block 66. It is advantageous for the sensor platform diameter to be one-half of the low frequency wavelength, the advantages of which will be made clear below.

Figure 7:
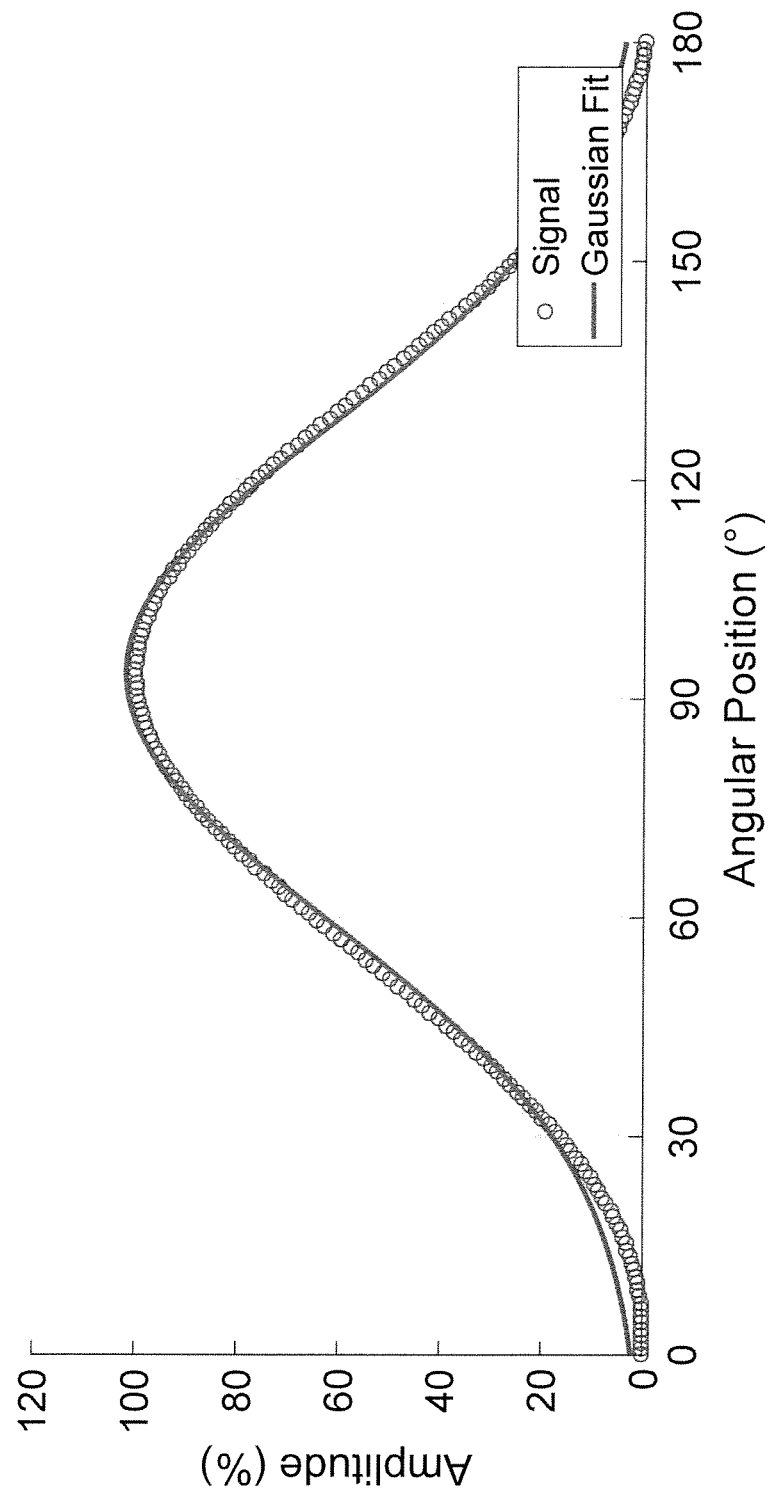
FIG. 7 shows the response rate of an exemplary DOA sensor as a function of angle for one rotation.

FIG. 7 shows the response rate of an exemplary DOA sensor as a function of angle for one complete rotation of the antennas. In this example the RF wave from the transmitter is 1.5 GHz. The signals from the two elements in each antenna pair are multiplied together and the amplitude is measured. The resulting signal represents an interference pattern produced from the combination of the two signals as a function of the angular position of the DOA sensor. The central peak corresponds with the direction vector between the transmitter and the axis of rotation of the sensor in the 2D plane of rotation.

Referring back to the distances illustrated in FIG. 6, the distance between the transmitter and the $i^{th}$ receiver may be expressed as $N_i$ fractions of a wavelength. Perfectly constructive interference occurs when $$N_2 - N_1 = \mathbb{Z}$$

and the condition for perfectly destructive interference is $$N_2 - N_1 = \mathbb{Z} + 1/2,$$

where $\mathbb{Z}$ is any integer. Given the condition that the sensor base is half of the low frequency wavelength (e.g., for a low frequency of 1.5 GHz, the wavelength is 20 cm and the sensor base is 10 cm in diameter), constructive interference occurs once per revolution of the device for any transmitter-receiver distance, unless the transmitter is positioned on the sensor's axis of rotation. The location of the perfectly constructive interference corresponds to the direction vector between the transmitter and the axis of rotation in the 2D plane of rotation. Only a single (e.g., low) frequency wavelength is strictly necessary to make the direction vector determination. The addition of the second higher wavelength (e.g., 47 GHz) wave advantageously allows for more precise identification of the location of the central peak, but is not strictly required in all embodiments.

Figure 8:
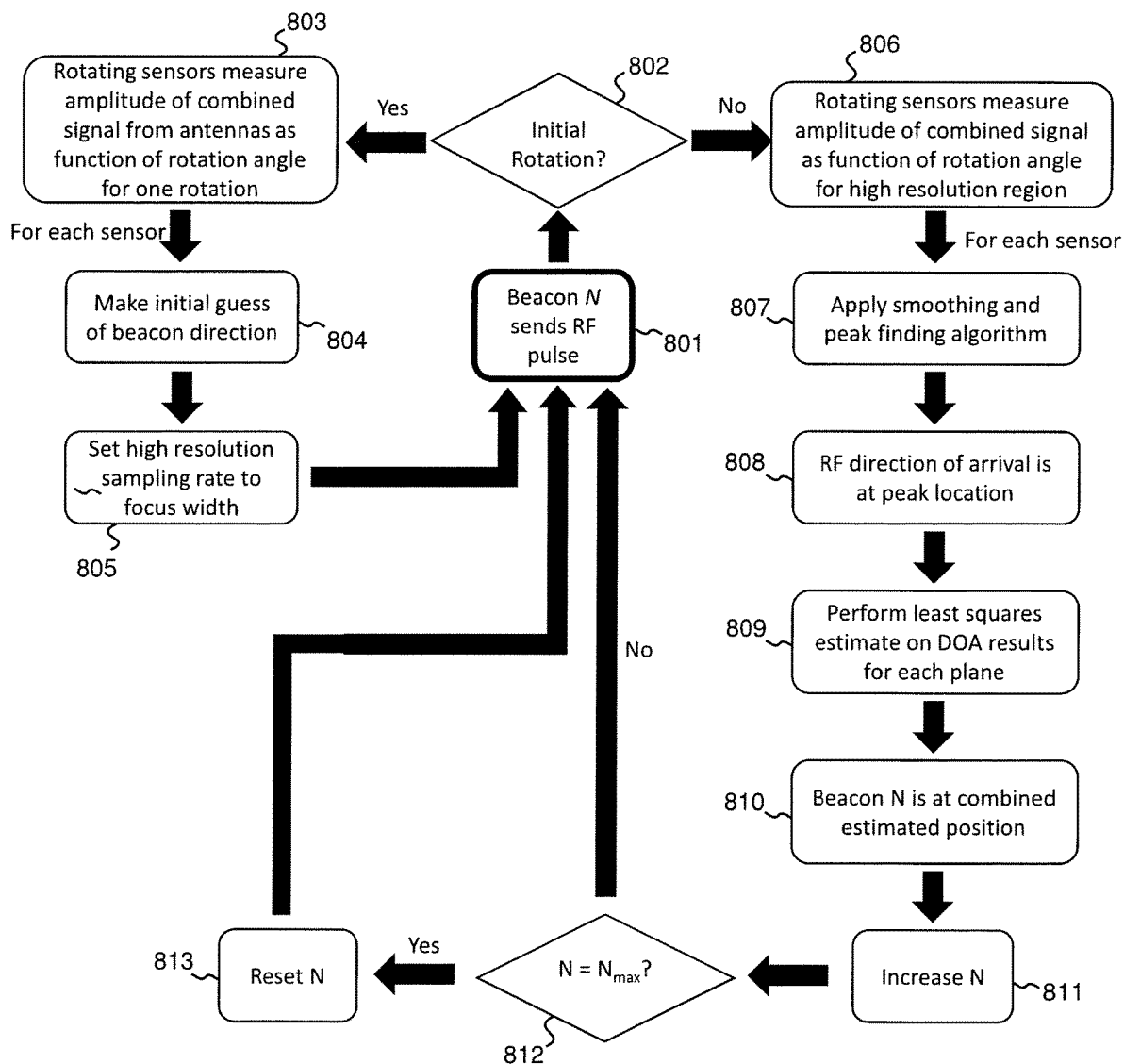
FIG. 8 is a flowchart demonstrating transmitter tracking by angulation of RF direction of arrival sensors.

FIG. 8 is a flowchart demonstrating transmitter tracking by angulation of RF direction of arrival sensors. Each transmitter emits a RF wave at a predesignated time or time window relative to the other transmitters (block 801). If a receiving sensor is on its initial rotation (block 802), the rotating sensor measures the amplitude of the combined signal from the antennas as a function of rotation angle for one rotation (block 803). For each sensor the number of peaks is counted in one half a rotation (block 804). A high resolution sampling rate is set to measure direction of arrival within a predefined margin (block 805). An exemplary margin is ±1°. For subsequent rotations of the sensors, the amplitude of the combined antenna signals are measured as a function of rotating angle for the high resolution region (block 806). For each sensor a smoothing and peak finding algorithm is applied (block 807). The direction of arrival is determined from the peak location in the combined interfered signal (block 808). A least squares estimate is performed on DOA results for each plane using all the sensors arranged in that plane (block 809). The original RF wave emitting transmitter/beacon is determined to be at a position based on the combination of estimates in separate planes (block 810). This determination process is executed for all transmitters (block 811 and 812), and then the process repeats (block 813) for continual monitoring of all transmitters over the course of the medical procedure (e.g., a radiotherapy session).

Figure 9A:
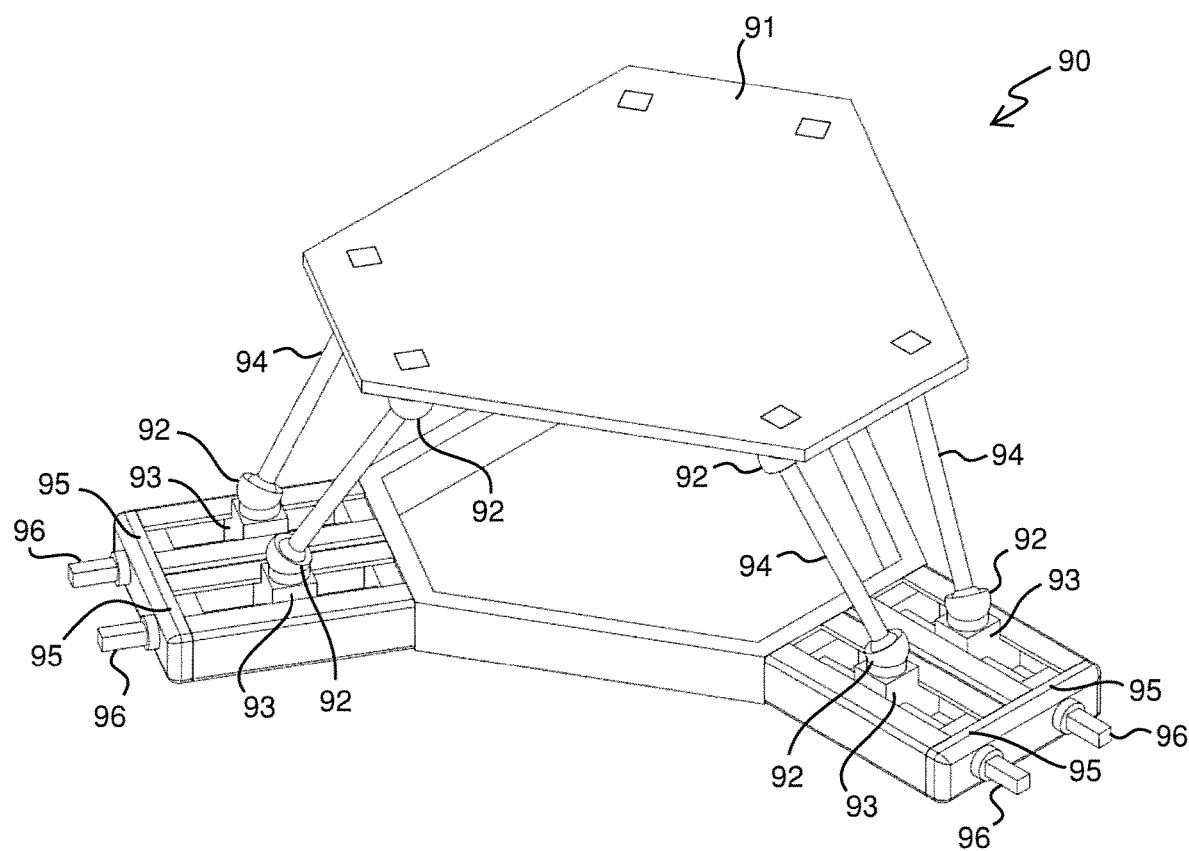
FIG. 9A is an isometric view of an exemplary positioning table.
Figure 9B:
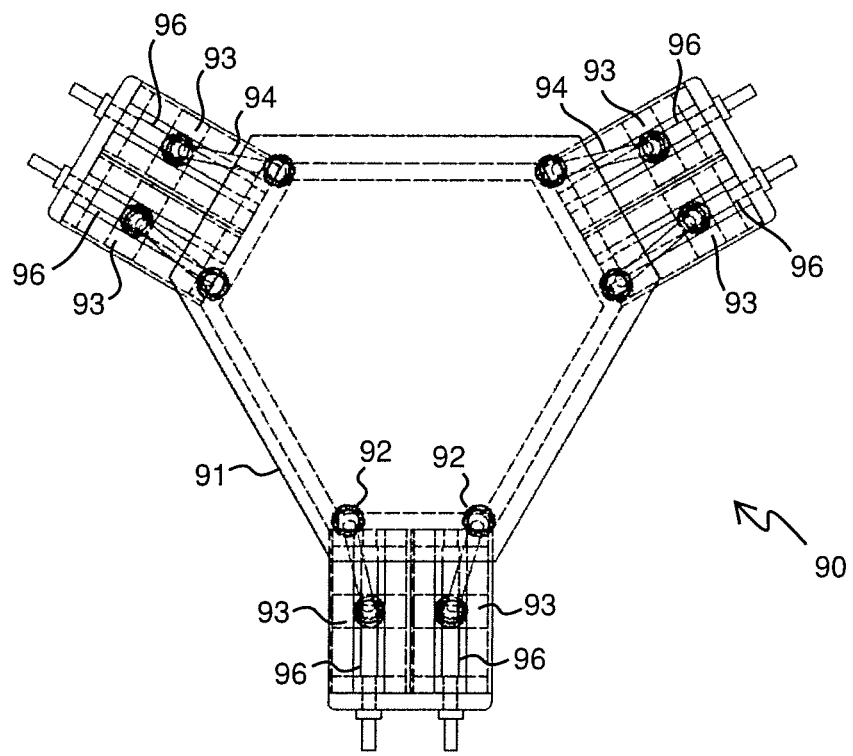
FIG. 9B is a top view of the table in FIG. 9A.
Figure 9C:
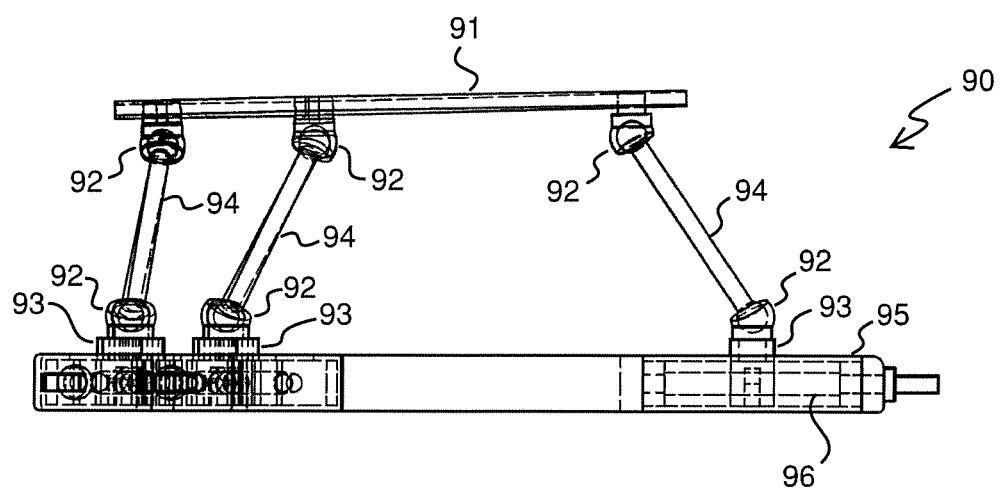
FIG. 9C is a side view of the table in FIGS. 9A and 9B.
Figure 10:
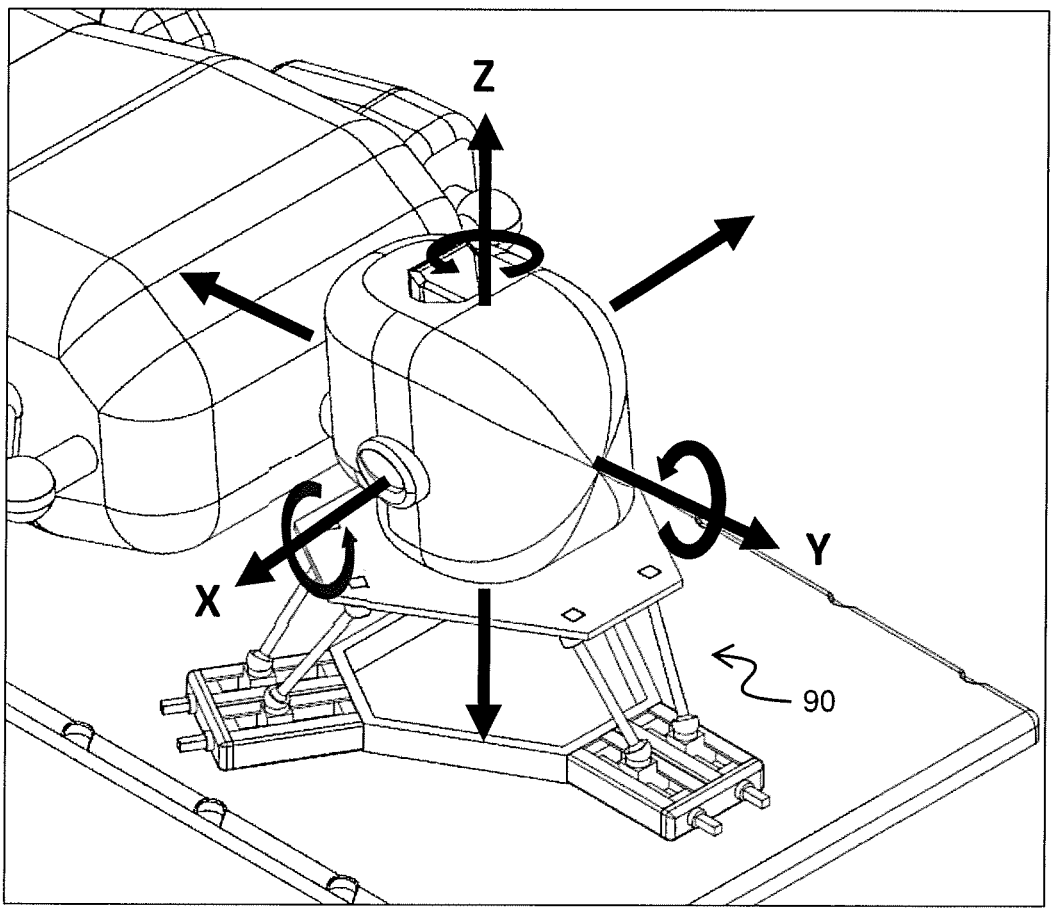
FIG. 10 shows a geometric reference system for describing the six degrees of freedom of an exemplary positioning table.

FIGS. 9A, 9B, and 9C show an example mechanical positioning table 90, and FIG. 10 shows a geometric reference system for describing the six degrees of freedom of an exemplary positioning table 90. The table allows movement in at least six independent degrees of freedom: translation along and rotation about the two orthogonal horizontal axes and one vertical axis. The axes are shown in FIG. 10 and may be defined such that the y-axis lies in the inferior-to-superior direction and rotations about the y-axis are referred to as roll; the x-axis lies in the left-to-right direction and rotations about the x-axis are referred to as pitch; and the z-axis lies in the posterior-to-anterior direction and rotations about the z-axis are referred to as yaw, assuming that a patient is in a standard supine position.

FIG. 9A is an isometric view of a positioning table 90, FIG. 9B a top view, and FIG. 9C a side view. The table 90 is preferably made from components such as plastic and/or carbon fiber to ensure compatibility with radiographic imaging systems, magnetic resonance imaging systems, and any external beam radiotherapy delivery. The positioning table 90 comprises a plate 91 which may be, for example, hexagonal, round, elliptical, square, or rectangular in shape. The plate 91 provides a support surface for the patient, in particular a part of the patient such as the patient's head. The plate 91 may be made of carbon fiber, for example. The plate 91 is shown as substantially flat but may take alternative shapes such as a curved surface or a combination of different surface contours. Attached to the plate 91 are joints 92 below each corner. The joints 92 are demonstrated as ball and socket type joints, although alternative joints providing the necessary two degrees of rotational freedom (e.g., pitch and yaw) may be used in differing arrangements. According to an exemplary embodiment, each of six joints 92 connect the plate 91 to a corresponding linkage (e.g., a rigid bar) 94 for a total of six linkages 94, grouped into three pairs. The linkages 94 are made of, for example, acrylonitrile butadiene styrene (ABS). The six linkages 94 in FIGS. 9A-9C are equal in length, although alternative arrangements may have bars 94 of differing lengths. Whereas one end of the linkage 94 is connected to the plate 91 with a joint 92, the opposite end of the linkage 94 is connected to a gliding or sliding base block (i.e., a glider or slider) 93 also with a joint 92. Each gliding base block 93 is mounted in its own dedicated track 95. The exemplary tracks 95 are linear and arranged in pairs extending radially from a common center, separated by 120°. The tracks have fixed positions relative to one another. This fixed configuration is provided in table 90 by a baseplate or frame. Each gliding base block 93 is attached to a mechanism which moves the gliding base block along the linear track, which is connected to a drivetrain and is subsequently turned externally by stepper motors. The sliding blocks may be attached to, for example, a worm gear or, alternatively, a chain and sprocket system for mechanical robustness. Other mechanisms may also be used. The base blocks 93 are devices that are able to maintain precise positions in the tracks 95 and yet move accurate and precise amounts when driven to do so by a control device.

In some embodiments, the positioning table 90 is controlled by motors such as conventional stepper motors such as a NEMA 17. While stepper motors like the NEMA 17 have metal components and are not imaging compatible, the table is configured with placement of the motors outside of the treatment field. In a physical prototype, the motors were controlled through a DAQ using a LabVIEW (National Instruments Corp., Austin, Tex.) interface. The stepper motors turn the transmission rods 96 suspended in the tracks, transferring the rotational motion of the motors into linear motion of the sliders 93. The sliding blocks 93 may be driven simultaneously or consecutively. The transmission rods 96 are made of nylon or similar material. The 6D position of the plate 91 may then be calculated by inverse kinematics based on the exact positioning of the six sliders 93 along their respective linear tracks 95. One or more computers control the motors to adjust the position of the plate 91 in response to a detection of the patient's actual position deviating from a reference position. The plate 91 is moved such that a difference between the actual position and reference position is reduced, preferably to substantially zero. In other words, the plate 91 counter effects patient movement to maintain an actual position that corresponds to or is identical with the reference position.

It is desirable that an entirety of the positioning table 90 is completely metal-less (e.g., devoid of any metal parts). Indeed, the various components of the transmission table (e.g., one or more, or all, of the plate, sliding blocks, linear tracks, linkages, and joints) may comprise or consist of ABS, nylon, polycarbonate, CFRP, PTFE, PLA, acetal resin, other plastics, or some combination thereof.

Figure 11:
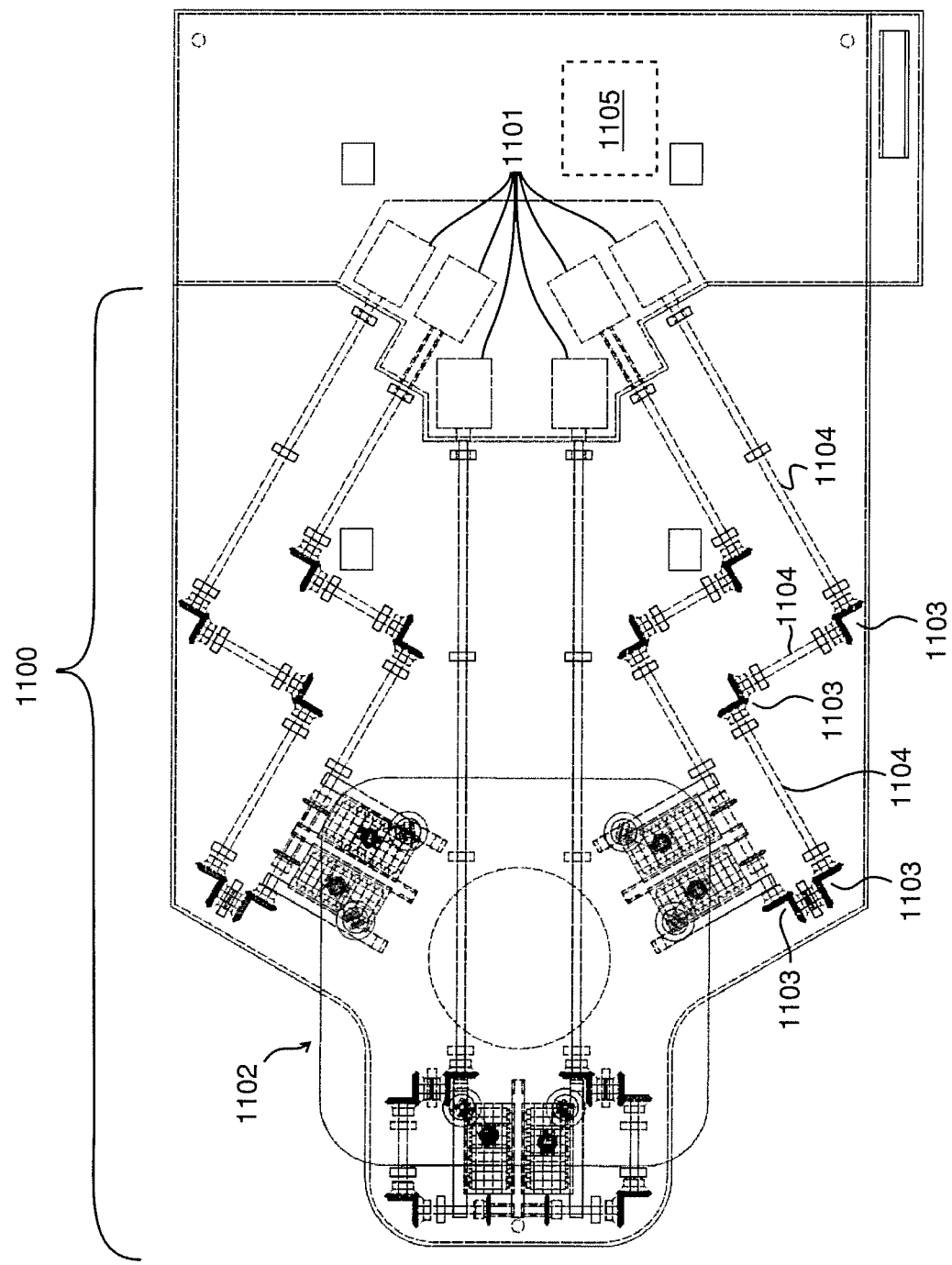
FIG. 11 shows an exemplary powertrain connecting external motors to a positioning table.

FIG. 11 shows an exemplary powertrain system 1100 connecting external motors 1101 to a positioning table 1102. The powertrain system 1100 illustrated in FIG. 11 includes six powertrains, each corresponding with one of six stepper motors 1101. Each powertrain is a train of gears 1103 and shafting 1104 transmitting power from a stepper motor to the mechanism being driven, which in this case is a base block. The powertrains connect the external stepper motors with the base blocks such that rotational motion of a stepper motor causes rotational motion of a transmission rod which causes a base block to translate along its linear track, thereby changing a position of one or more of the linkages. Changing a position of a linkage in turn changes a position or orientation of the plate. The plate may is moved with one or more of x-axis translation, y-axis translation, z-axis translation, rotation about the x-axis, rotation about the y-axis, and rotation about the z-axis by driving one or more of the base blocks simultaneously or consecutively. The motors 1101 and the positioning table 1102 are driven by a control device 1105. The gears 1103 and shafts 1104 of the powertrain system can be positioned under one or more supports 27 (see FIG. 2A) and allow the motors 1101 and control device 1105 to be positioned at a considerable distance from the treatment or imaging region, which is generally inside the boundaries given by the edge of the plate of the positioning table 1102.

Figure 12A:
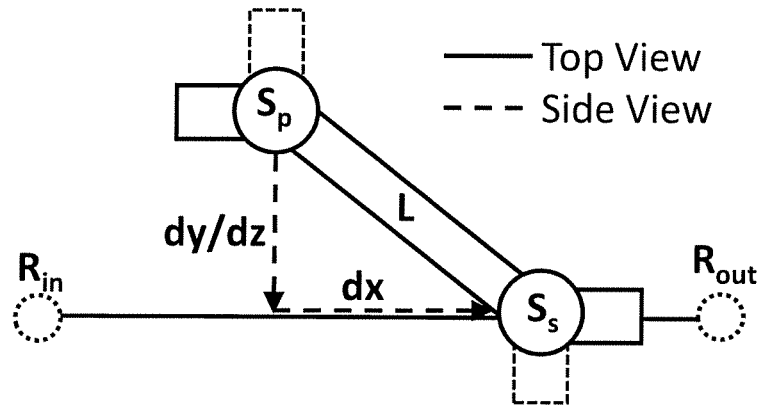
FIGS. 12A, 12B, and 12C demonstrate the geometry of an exemplary positioning system.
Figure 12B:
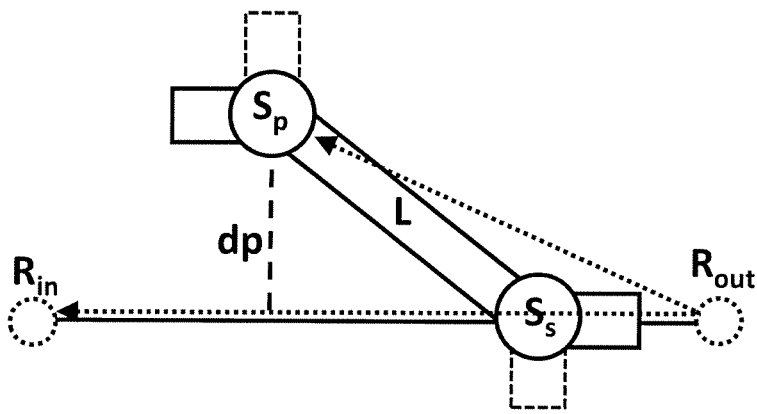
Figure 12C:
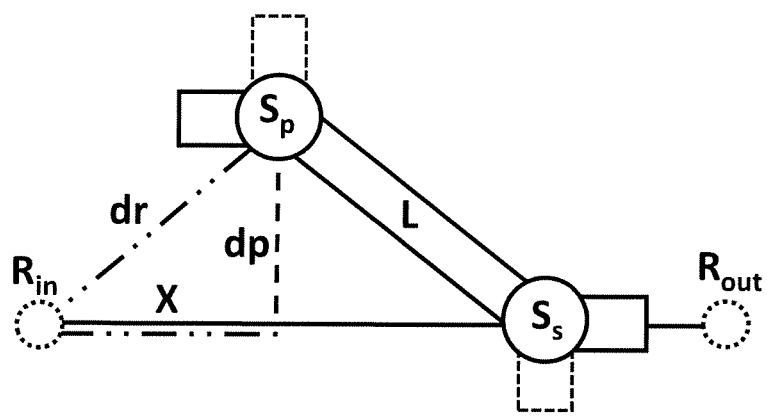

FIGS. 12A, 12B, and 12C demonstrate the geometry of an exemplary positioning system. The inverse kinematics algorithm used the target 6D coordinates to calculate the necessary linear position for each slider. Let $S_p$ be the set of 3D coordinates (x,y,z) for each of the six sockets attached to the plate as defined in the manufacturing process relative to the center of the top surface of the plate. The target positions for this set of sockets are found by $$S_p = R_z(\gamma) R_y(\beta) R_x(\alpha) S_{p,0} + T(x,y,z) \quad (1)$$

where $R_z$, $R_y$, and $R_x$ are the standard rotation matrices about the z, y, and x axes, respectively, and T is the translation vector for the reference position of the plate. The length of the linkage connecting the sockets on the plate and the sockets in the sliders is of known length, but is also defined by a composition of component vectors in an arbitrary reference frame:

$$S_p - S_s = L^2 = \Delta x'^2 + \Delta y'^2 + \Delta z'^2 \quad (2)$$

where $S_s$ is the set 3D coordinates (x,y,z) for each of the six sockets attached to sliders. By construction, the vector along the x' direction represents the projected displacement between the plate and slider sockets along the slider's path of motion on its rail (i.e., track), while the vectors in the y' and z' directions represent the projected displacements in the orthogonal horizontal and the vertical directions, respectively. The $\Delta y'$ and $\Delta z'$ vectors may then be combined into a single vector which represents the projected displacement between the sockets in the plane perpendicular to the direction of the slider's rail, and may be represented by $$\Delta p^2 = \Delta y'^2 + \Delta z'^2 \quad (3)$$

This perpendicular vector may be found through the directed area product of the known vectors along the slider's rail and between a known point on the slider's rail and the corresponding plate socket, both of which are specified in the initial geometry $$\Delta p = \frac{\|(R_{out} - R_{in}) \times (S_p - R_{in})\|}{\|(R_{out} - R_{in})\|} \quad (4)$$

$R_{out}$ represents a reference point on the rail distal to the slider, while $R_{in}$ represents a reference point on the rail medial to the slider. From this construction, the projected displacement along the rail between the sockets, $\Delta x'$, may be found by rearranging equation 2. The geometric relationship between the rail and the corresponding plate socket may further be specified by $$\Delta r = \|S_p - R_{in}\| \quad (5)$$

Using this vector, the distance between the inner reference point and the start of $\Delta x'$ may be calculated using the relationship $$\Delta X'^2 = \Delta r^2 - \Delta p^2 \quad (6)$$

The position of the slider along the rail is then found by the addition of the distances $$P = \Delta X' + \|\Delta x'\| \quad (7)$$

An exemplary positioning table is configured to achieve any translational motion within the bounds of +1.0 cm in any direction from the default resting position as well as ±2.0° of rotation motion around any axis at any valid translational position.

Example 1

A generic prototype of a sensor comprising a rotating array platform and antenna elements was simulated on a computer using MATLAB (Mathworks, Natick, Mass.). A Monte Carlo simulation was used to estimate the accuracy of a least squares solution. The simulation estimates the magnitude of the positioning error based on the number of sensors in the network and the angular resolution of the sensors.

Methods

Direction of Arrival Measurements

The simulation was based on the external sensor system geometry illustrated and described with FIGS. 5A and 5B. The transmitters emitted sine waves with a main frequency of 1.5 GHz, selected as a compromise between antenna spatial constraints and available spectra. In the simulation, the transmitter was placed at origin and the center of the sensor was placed at 2 meters away in the horizontal plane and 1 meter above the plane of the transmitter.

Because the main frequency component has a wavelength equal to twice the length of the sensor's diameter, the resultant interfered signal oscillates at the rate of the sensor rotation, and the angular position of the peak corresponds to the direction of arrival. Were an optional secondary high frequency component used, it would create a secondary oscillation with a predictable pattern that may facilitate identification of the center of the peak.

FIGS. 13A and 13B show the spatial geometry of a single sensor at selected locations and the sensor's signal response for one-half revolution. The central peak of the signal shape represents the direction used for the narrow search. FIG. 13A shows the transmitter at a position of 90° with respect to the coordinate system. FIG. 13B shows the transmitter at a position of 135° with respect to the coordinate system.

One-half of a sensor rotation may be used as a coarse measurement to find the direction to the nearest 5°, and a high-resolution scan may be performed over a much smaller arc to find the direction at the limitations of the method (~0.05°). In the simulation, the following equation creates a time-dynamic transmitted wave:

$$(t) = A_1 \sin(2\pi f_1 t + \varphi_1) + A_2 \sin(2\pi f_2 t + \varphi_2) \quad (8)$$

where $A_1$ and $A_2$ are the respective amplitudes of the two waves, $f_1$ and $f_2$ are the respective frequencies of each wave, t is the sampled point in time, and $\varphi_1$ and $\varphi_2$ are the respective initial phases of each wave. The transmitted wave is sampled at 150 THz over a 33 nS pulse. This corresponds to 25 wavelengths of the frequency of 1.5 GHz ($2.5 \times 10^5$ points). The starting phases of the wave components were chosen from a uniform random distribution between 0 and 2π. The amplitudes of both waves were assumed equal in strength. The wavelength of the main frequency component is calculated according to the speed of light in air, and is termed as the carrier wavelength.

Vector analysis defines the location of the transmitter as point t in 3D space. The center of a given sensor is defined as point s, and the angular position of the $i^{th}$ antenna in the plane of the sensor's rotation is defined as $\alpha_1$. The vector (V) between the transmitter's location and the center of the sensor is defined as:

$$\hat{V} = s - t \qquad (9)$$

The vectors from the center of the sensor to the $i^{th}$ antenna receiver was then calculated for angular positions (j):

$$\hat{C} = R^*[\cos \alpha_{i,j}, \sin \alpha_{i,j}, 0] \qquad (10)$$

The distance between the transmitter and each $i^{th}$ receiver at every $j^{th}$ sampled angular position was then found as the magnitude of the vector connecting between the transmitter and each receiver:

$$d_{i,j} = \|\hat{V} + \hat{C}_{i,j}\| \qquad (11)$$

This distance is then converted to fractions of the carrier wavelength, $m_{i,j}$. At each angular position j, each receiver reads the transmitted signal after the respective number of wavelengths of the transmitted signal, $m_{i,j}$+M, for n wavelengths, where M represents the minimum number of wavelengths to wait before the signal is read. This "wait" parameter was included to ensure the receivers did not attempt to read the signal before the first index in the transmitted signal. In this simulation, the parameters of M=5 and n=10 were used.

This process simulates the phase difference ($\varphi$), measured between the two receiving antennas of a single sensor at the same instant. Uniform Gaussian white noise is added at a given signal-to-noise ratio (SNR). In this simulation, the SNR value of 2 was used assuming a poor RF environment. The signals were then multiplied and the resultant amplitude was recorded and plotted against each sensor angle $\alpha_j$. A median filter is used to help overcome the noisy environment. A peak-finding algorithm is then used to identify the locations of the signal peaks. This process was repeated over 5000 iterations in a 4° search space of the simulated transmitter's known position to judge the accuracy of the direction finding algorithm.

Angulation Uncertainty Estimation

Figure 14A:
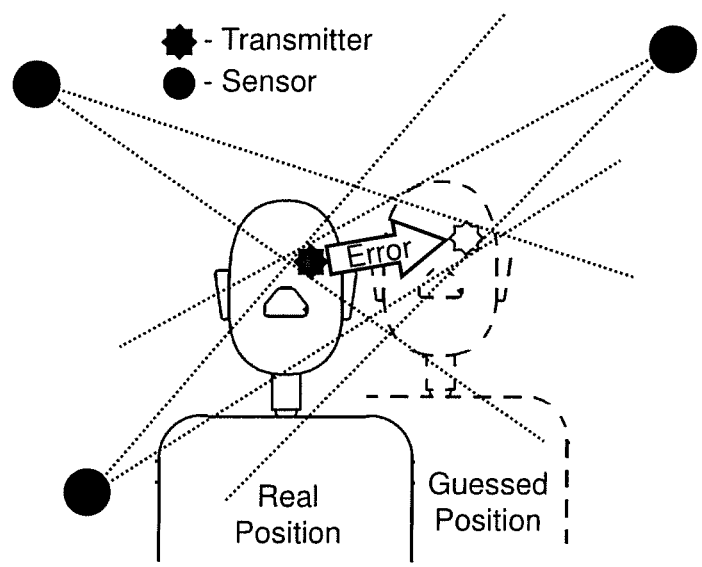
FIG. 14A shows a rationale for creating the Monte Carlo simulation: angular uncertainty exists in direction measurements, which can lead to errors in the localization process.

FIG. 14A illustrates the limitation of individual sensors called angular uncertainty, and how it can cause an error in the measured position of a transmitter. Some angular uncertainty is generally inherent in direction measurements, and it can lead to errors in the localization process. FIG. 14A shows three sensors (circles) arranged around a transmitter (star) that is affixed to a patient. Beams show the angular uncertainty for each respective sensor. Two transmitter positions are shown, one which corresponds with the real position of the transmitter and patient and one which corresponds with a guessed position of the transmitter and patient. Both the real position and guessed position are within the beams of all three sensors. Thus, the sensors cannot perceive a difference between the two positions illustrated. Both would be perceived as accurate within the margin of error resulting from the angular uncertainty of the three sensors. In general, a larger number of sensors reduces the illustrated Error as compared to a smaller number of sensors.

Multiple sensors are generally required to localize each transmitter's signal in three-dimensional space. In this simulation, the external sensor locations were randomly distributed in a room-sized hemispherical shell, centered at the simulated transmitter, to investigate the relationship between the number of direction measurements and estimation. The polar and azimuthal coordinates of each sensor was selected in a uniform 2π space. The radial distance from the transmitter to each receiver was taken from a uniform distribution between 3.5 and 4.5 meters, which is an approximate size of a treatment room. The relationship between the angular resolution of the sensors and the accuracy of the position estimate was investigated by performing multiple iterations of estimation based on the same physical setup but varying the magnitude of the uncertainty in the angular measurement.

Figure 14B:
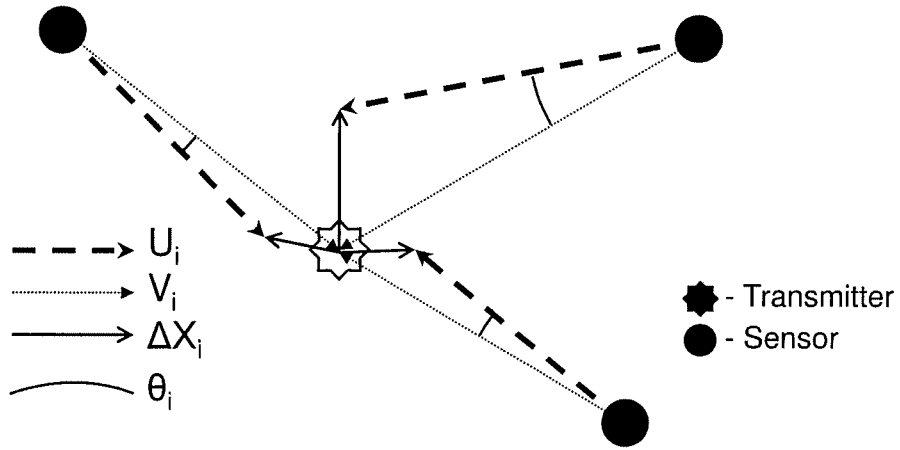
FIG. 14B illustrates part of the process of the Monte Carlo simulation.

The relationship between the number of sensors and the physical arrangement of the sensor was also investigated. The initial 3D direction vectors between each sensor and transmitter was calculated as:

$$\hat{V}_i = \frac{s_i - p}{\|s - p\|} \qquad (12)$$

where the positions $s_i$ represents the position of the $i^{th}$ sensor and p represents the position of the transmitter. In order to simulate uncertainty in the direction of arrival measurement spatial variation, $\Delta X_i$ was added to the transmitter's position for direction of arrival measurement according to a 3D Gaussian distribution of width $\sigma_j$ and direction vectors were calculated again (FIG. 14B). Values of $\sigma_j$ were varied exponentially between $(1.5)^2$ and $(1.5)^{28}$ to observe a wide range of angular resolutions.

$$\hat{U}_{i,j} = \frac{s_i - (p + \Delta \hat{X}_{i,j}(\sigma_j))}{\|s_i - (p + \Delta \hat{X}_{i,j}(\sigma_j))\|} \qquad (13)$$

A least squares estimate of the position, $t_j$, was calculated based on these new direction vectors for each magnitude of angular resolution $\sigma_j$.

$$t_j = (\Sigma_i I - \hat{U}_{i,j} \hat{U}_{i,j}^T)^{-1} (\Sigma_i (I - \hat{U}_{i,j} \hat{U}_{i,j}^T) s_i) \qquad (14)$$

where I represents a 3×3 identity matrix. The magnitude of the error in the estimated position was then found for each level of $\sigma_j$.

$$\text{Error}_j = \|t_j - p\| \qquad (15)$$

For each level of $\sigma_j$, the average angular miss was calculated by taking the dot product between the true direction vectors from the transmitter and sensors and the simulated miss.

$$\overline{\theta_j} = \overline{\cos^{-1}(\hat{U}_{i,j} \cdot \hat{V}_i)} \qquad (16)$$

Figure 14C:
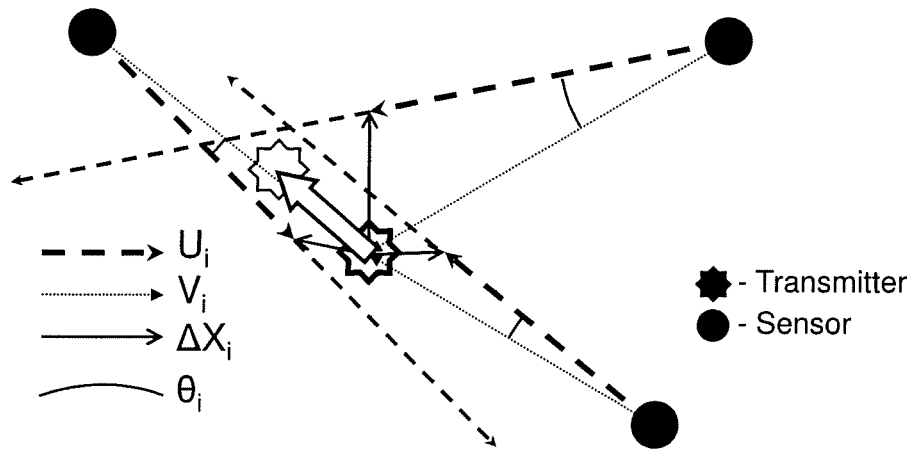
FIG. 14C shows the continued process of the Monte Carlo simulation.

The mean angular miss θ serves as a surrogate for angular uncertainty and was compared to the Error in estimated position for each $\sigma_j$ (FIG. 14C). This process had 5000 iterations for each $\sigma_j$ to obtain statistically acceptable ranges of error for a given angular uncertainty. The number of receivers on each row varied by 5, 50, and 500 in the network. This calculation was performed to observe the effect of increasing the number of vectors available for angulation analysis.

FIG. 14B illustrates a portion of the process of the Monte Carlo simulation described above. In brief review, angular uncertainty, $\theta_i$, is created by adding a vector, $\Delta X_i$, to the true vector between sensor and transmitter, $V_i$, resulting in a simulated mismeasurement of direction, $U_i$. The vectors $\Delta X_i$ are randomly taken from a 3D Gaussian distribution.

FIG. 14C illustrates a continued portion of the process of the Monte Carlo simulation described above. In brief review, a least squares calculation was used to find the best-fit intersection of the mis-measured direction vectors, $U_i$, and the error was taken as the difference between the intersections of the mis-measured $U_i$ vectors and the intersection of the true $V_i$ vectors. The error was compared to the average angular uncertainty, $\theta_i$.

Results

Direction of Arrival Measurements

Figures 15A, 15B:
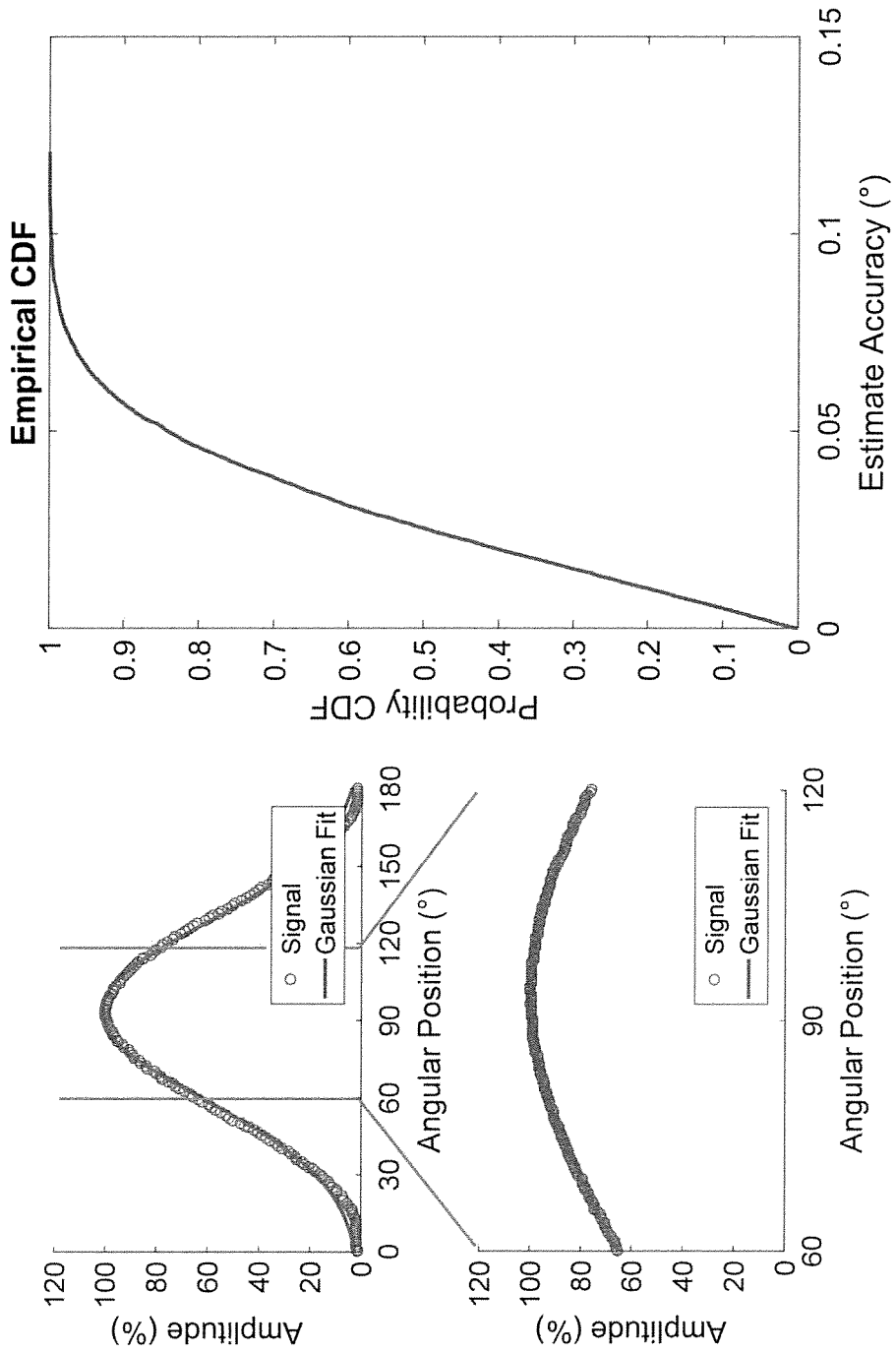
FIG. 15A shows, in the top plot, a sensor signal response for one-half rotation when the transmitter was located at 93.526° (a typical angle) with respect to the coordinate system with SNR=2, and in a bottom plot, a signal response for a 60° high resolution scan area when the transmitter was at 93.526° with respect to the coordinate system with SNR=2.
FIG. 15B shows a cumulative probability distribution of the results of the direction-finding program used on the high resolution scan area in FIG. 15A.
Figure 16:
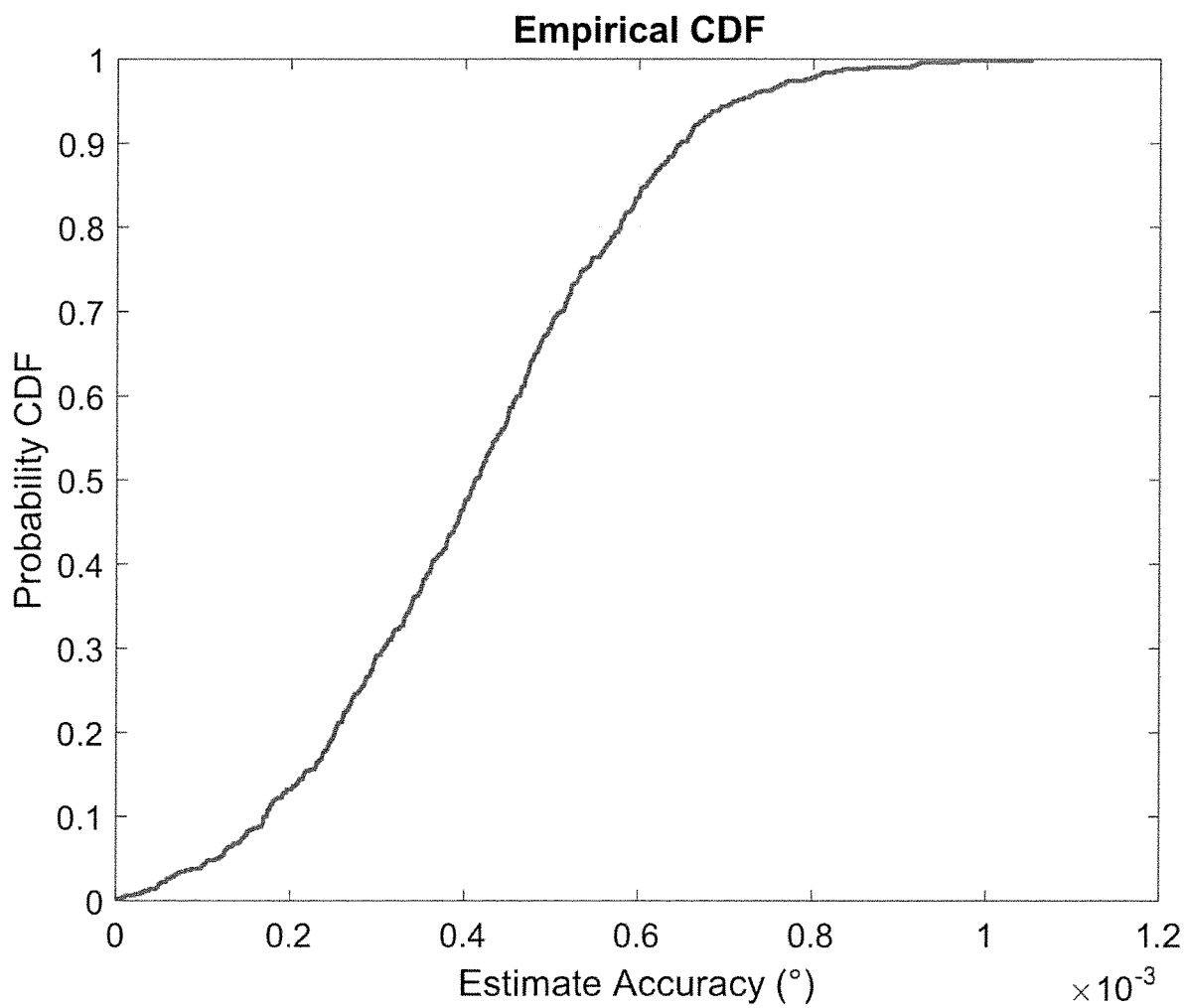
FIG. 16 shows a cumulative probability distribution of the results of the direction-finding program used on a high resolution scan area in a low noise environment (SNR=2000).

FIGS. 15A and 15B show the results of the simulation for direction of signal arrival. The top plot of FIG. 15A shows sensor signal response for one-half rotation when the transmitter was located at 93.526° with respect to the coordinate system with SNR=2. The bottom plot of FIG. 15A shows the signal response for the 60° high resolution scan area when the transmitter was at 93.526° with respect to the coordinate system with SNR=2. FIG. 15B shows a histogram of the results of the direction-finding program used on the high resolution scan area in the bottom plot of FIG. 15A. Over 5000 iterations, the program found the direction of the transmitter to with an accuracy of 0.0288°±0.0263° compared to ground-truth. FIG. 16 shows a cumulative probability distribution of the results of the direction-finding program used on a high resolution scan area in a low noise environment (SNR=2000). In this case accuracy was 0.000413°±0.00189°.

The measured data demonstrates that the product of the signals from two rotating receivers (antennas) of the sensor's rotating antenna array forms a signal that may be easily identified, which rises from a minimal value at 0° rotation (when the antennas are in line with the signal path) to a maximum value at 90° rotation (when the vector between the antennas is perpendicular to the signal direction). The signal then returns to a minimum value at 180°. The pattern repeats every 180° because the sensor has 2-fold rotational symmetry. The interference between 1.5 GHz signals creates a pattern as the antenna array platform rotates. The central peak of the signal corresponds to the direction of signal arrival, which may be located in angular space by the signal analysis. A peak-finding algorithm found the peak of the high-resolution signal. Based on 5000 iterations of this process, the peak corresponding to the direction of the transmitter was found to differ from the ground-truth direction by 0.0288±0.0263°.

Angulation Uncertainty Analysis

Figure 17A:
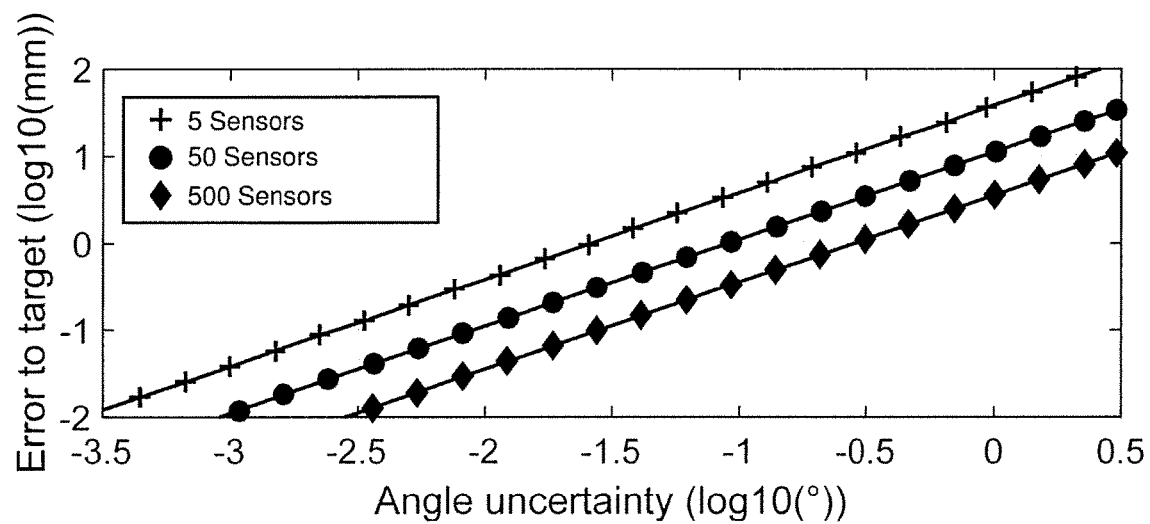
FIG. 17A shows the relationship between angular precision and error in least squares estimate of transmitter position.
Figure 17B:
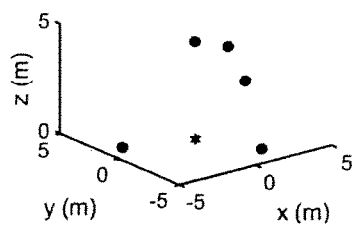
FIG. 17B is a spatial distribution of sensors for a 5-sensor case.
Figure 17C:
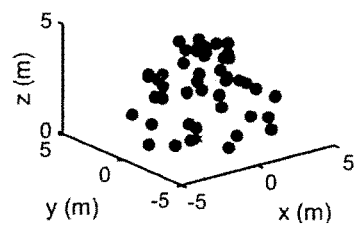
FIG. 17C is a spatial distribution of sensors for a 50-sensor case.
Figure 17D:
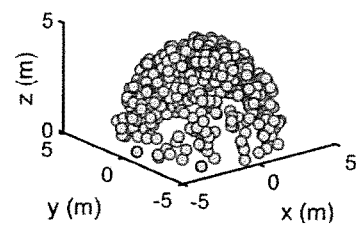
FIG. 17D is a spatial distribution of sensors for a 500-sensor case.

FIG. 17A shows the relationship between angular precision and error in least squares estimate of transmitter position. Better results are closer to the bottom of the graph. FIG. 17B shows a spatial distribution of sensors for the 5-sensor case. FIG. 17C shows a spatial distribution of sensors for the 50-sensor case. FIG. 17D shows a spatial distribution of sensors for the 500-sensor case.

The relationship between the angulation uncertainty of direction of signal arrival and the mean error of the position estimate is linear, as illustrated by FIG. 17A. The result shows that increased number of receivers improves the position estimation for a given angular resolution, but follows a logarithmic rate of improvement. The logarithmic plot in FIG. 17A shows that the slopes of lines are parallel, which means that the rate of estimation improvement with respect to angular resolution depends on the number of direction estimates. The example system aims the tracking sensitivity less than 1 mm, considering the typical dose margins in conformal radiotherapy. Therefore, the direction of arrival sensors requires an angular resolution near 10-1.4 degrees (~0.04° to achieve the ideal accuracy (FIG. 17A) based on the assumption that an exemplary design may include ~50 sensors (e.g., 40-60 sensors, 50 sensors, etc.). The consistency criterion is based on exceeding the 2σ worst-case scenario. Given that this estimate is an order of magnitude estimate, it's concluded that the simulated sensor accuracy and precision is sufficient.

DISCUSSION

In a clinical environment, RF-based tracking equipment is largely untested. Potential RF reflectors include radiotherapy linear accelerators and simulation CT scanners. In this work, a RF localization system was introduced for accurate tracking of patient motion in radiotherapy, which would provide high accuracy and robustness even in poor SNR setting using RF waves. In the example embodiment, the system also calls for the use of components that operate in the K-band of the electromagnetic spectrum, which are not widely available in normal commercial channels and less investigated in scientific and engineering literature.

Based on the results of the example, it was observed that three parameters can reduce the error in the positioning estimation: improving the angular resolution, increasing the number of sensors, and reducing the distance between the each transmitter on a patient and sensor in the external system. Due to practicality reasons, the number of sensors is generally constrained to be less than about 100 total, and the sensor-transmitter distance is constrained by the room geometry. Therefore, this example focuses a great amount of effort into methods that can improve the angular resolution of the direction of arrival analysis software. Based on standard room sizes, and assuming that on the order of 50 sensors will be used, it's estimated that an angular resolution near 0.04° is necessary to achieve position estimate errors less than 1 mm. Achieving 0.01° resolution may be possible with strong peak detection algorithms, even in poor SNR environments.

Example 2

Structural Finite Element Analysis (FEA) was performed on a CAD model of the positioning table shown in FIGS. 9A-9C, 10, and 11 using Autodesk Inventor Professional 2017 (Autodesk Inc., San Rafael, Calif.). The device was simulated to assess the durability of the plastic model under the weight of a patient. A 45 lb load was simulated on the plate, which is about three times the average weight of a human head to account for a reasonable factor of safety. Fixed, rigid constraints were placed on the bottom surfaces of the slider channels. The device was simulated in two positions, one with all sliders at their most proximal positions to the center of the plate, and one with all sliders at their most distant settings, 5 cm away. The following table indicates component characteristics.

| Component | Material | Density (g/cm³) | Modulus of Elasticity (GPa) | Yield Strength (MPa) |
| --- | --- | --- | --- | --- |
| Plate | CFRP | 1.44 | 133 | 300.0 |
| Sockets | ABS | 1.05 | 2.2 | 20.0 |
| Linkage | ABS | 1.05 | 2.2 | 20.0 |

-continued

| Component | Material | Density (g/cm³) | Modulus of Elasticity (GPa) | Yield Strength (MPa) |
|---|---|---|---|---|
| Glider | ABS | 1.05 | 2.2 | 20.0 |
| Track | PVC | 1.41 | 3.4 | 46.5 |
| Worm Gear | Nylon | 1.13 | 2.9 | 82.7 |
| Baseplate | Polycarbonate | 1.13 | 2.3 | 62 |

The radio-compatibility of the prototype was tested by placing the device without stepper motors into a clinical treatment planning simulation CT scanner. The average Hounsfield Unit (HU) of each major component was also measured. The HU noise of each component was also measured.

The accuracy and reproducibility of the motion of the device were tested in a radiation therapy treatment room. The ground-truth 6D position was measured using infrared reflective markers and the optical camera of an ExacTrac system. The resting state of the device was defined as the point at which all linear sliders were the same distance from the central brace of the device and the measured center of the top surface of the plate was 8 cm above the surface of the table, as measured by the optical distance indicator on the linear accelerator. The axes of motion of the device were aligned with the axes of measurement of the ExacTrac system within ±0.1°.

The device is designed to achieve any translational motion within the bounds of ±1.0 cm in any direction from the default resting position as well as ±2.0° of rotation motion around any axis at any valid translational position. The reproducibility of motion of the device was tested by instructing to the device to move repeatedly between a specified position and the home coordinate and measuring the achieved position at both points. This process was repeated for 10 trials and the accumulated drift was measured.

The reproducibility of motion of the device was tested by instructing to the device to move repeatedly between a specified position and the home coordinate and measuring the achieved position at both points. This process was repeated for 10 trials and the accumulated drift was measured.

The above described tests showed favorable results in all categories: performance under maximum loading conditions, imaging compatibility, motion accuracy, and motion reproducibility.

In the preceding figures, each block in the flowchart or block diagrams may represent a module, segment, or portion of instructions, which comprises one or more executable instructions for implementing specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The present invention may include a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network (LAN), a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, which describe signal processing or signal analysis can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart in FIG. 8, for example, illustrates functionality and operation of possible implementations of systems, methods, and computer program products according to various embodiments of the present invention.

It should be appreciated that the illustrative embodiments described and illustrated herein are non-limiting, and aspects of different illustrative embodiments may be combined, added, or interchanged with aspects of other embodiments. As an example, aspects of sensors 25, 37, 45, 55, and 65 of their respective figures may be combined in various combinations in the practice of the invention. Furthermore, while many exemplary embodiments described herein are directed to applications in medical fields, the invention is not inherently limited to medical applications. Aspects of embodiments of the invention such as but not limited to localization systems and methods or positioning tables may be employed in other capacities and fields. In such circumstances discussions of a patient may be treated as being made with respect to a more general subject, such as a person or object. While exemplary embodiments of the present invention have been disclosed herein, one skilled in the art will recognize that various changes and modifications may be made without departing from the scope of the invention as defined by the following claims.

We claim:

1. A positioning table for use during a medical procedure, comprising:
   a plate for providing a support surface for a specific part of a patient's body;
   a plurality of sliding blocks mounted in linear tracks separated into parallel pairs;
   a plurality of linkages that connect the plate to the sliding blocks, wherein the linkages connect to the plate and the sliding blocks with joints having at least two degrees of rotational freedom; and
   a powertrain connecting external motors with the sliding blocks such that rotational motion of a motor causes a sliding block mounted in the linear track to translate along the track, thereby changing a position of one or more of the linkages,
   wherein the plate, sliding blocks, linear tracks, linkages, and joints are metal-less.

2. The positioning table of claim 1, wherein the sliding blocks, linear tracks, linkages, and joints consist of ABS, nylon, polycarbonate, CFRP, PTFB, PLA, acetal resin, other plastics, or some combination thereof.

3. The positioning table of claim 1, wherein the positioning table has at least six degrees of freedom.

4. The positioning table of claim 3, wherein the positioning table is configured such that the plate is moved or moveable with one or more of x-axis translation, y-axis translation, z-axis translation, rotation about the x-axis, rotation about the y-axis, and rotation about the z-axis by driving one or more of the sliding blocks.

5. The position table of claim 1, wherein the plate is configured to support a patient's head.

6. The positioning table of claim 1, wherein the plate is flat, curved, or a combination of different surface contours.

* * * * *